(12) United States Patent
Couto et al.

(10) Patent No.: US 9,885,721 B2
(45) Date of Patent: Feb. 6, 2018

(54) PD-L1 ANTIBODIES AND USES THEREOF

(71) Applicant: Spring BioScience Corporation, Pleasanton, CA (US)

(72) Inventors: Fernando Jose Rebelo do Couto, Pleasanton, CA (US); Zhiming Liao, Livermore, CA (US); Yifei Zhu, San Jose, CA (US)

(73) Assignee: Spring BioScience Corporation, Pleasanton, CA (US)

(*) Notice: Subject to any disclaimer, the term of this patent is extended or adjusted under 35 U.S.C. 154(b) by 0 days.

(21) Appl. No.: 14/725,953

(22) Filed: May 29, 2015

(65) Prior Publication Data

US 2015/0346208 A1 Dec. 3, 2015

Related U.S. Application Data

(60) Provisional application No. 62/069,420, filed on Oct. 28, 2014, provisional application No. 62/004,572, filed on May 29, 2014.

(51) Int. Cl.
*C07K 16/28* (2006.01)
*C07K 16/30* (2006.01)
*G01N 33/574* (2006.01)

(52) U.S. Cl.
CPC ... *G01N 33/57492* (2013.01); *C07K 16/2827* (2013.01); *C07K 16/2896* (2013.01); *C07K 2317/34* (2013.01); *C07K 2317/51* (2013.01); *C07K 2317/515* (2013.01); *C07K 2317/92* (2013.01); *G01N 2333/70596* (2013.01)

(58) Field of Classification Search
None
See application file for complete search history.

(56) References Cited

U.S. PATENT DOCUMENTS

| | | | |
|---|---|---|---|
| 5,922,855 A | 7/1999 | Liskay et al. | |
| 6,803,192 B1 | 10/2004 | Chen et al. | |
| 7,635,757 B2 | 12/2009 | Freeman et al. | |
| 7,754,208 B2 | 7/2010 | Ledbetter et al. | |
| 7,892,540 B2 | 2/2011 | Chen et al. | |
| 7,895,540 B2 | 2/2011 | Engin et al. | |
| 8,217,149 B2 | 7/2012 | Irving et al. | |
| 8,552,154 B2 | 10/2013 | Freeman et al. | |
| 8,981,063 B2 | 3/2015 | Chen et al. | |
| 2002/0028487 A1 | 3/2002 | La Thangue et al. | |
| 2009/0317368 A1 | 12/2009 | Chen et al. | |
| 2010/0203056 A1 | 8/2010 | Irving et al. | |
| 2011/0200620 A1 | 8/2011 | Chen et al. | |
| 2012/0039906 A1 | 2/2012 | Olive et al. | |
| 2013/0034559 A1 | 2/2013 | Queva et al. | |
| 2013/0309250 A1 | 11/2013 | Cogswell et al. | |
| 2014/0341917 A1 | 11/2014 | Nastri et al. | |
| 2014/0356353 A1 | 12/2014 | Queva et al. | |
| 2015/0071910 A1 | 3/2015 | Kowanetz et al. | |
| 2015/0346210 A1 | 12/2015 | Nitta et al. | |

FOREIGN PATENT DOCUMENTS

| | | |
|---|---|---|
| AU | 2012211347 A1 | 8/2012 |
| CN | 102250911 A | 11/2011 |
| CN | 102740887 A | 10/2012 |
| JP | 2012503984 A | 2/2012 |
| WO | 0139722 A2 | 6/2001 |
| WO | 2010036959 A2 | 4/2010 |
| WO | 2010077634 A1 | 7/2010 |
| WO | 2011041613 A2 | 4/2011 |
| WO | 2012003476 A2 | 1/2012 |
| WO | 2013079174 A1 | 6/2013 |
| WO | 2013172926 A1 | 11/2013 |
| WO | 2013173223 A1 | 11/2013 |
| WO | 2014022758 A1 | 2/2014 |
| WO | 2014100079 A1 | 6/2014 |
| WO | 2014165082 A2 | 10/2014 |
| WO | 2014165422 A1 | 10/2014 |
| WO | WO2014165082 A2 * | 10/2014 |
| WO | 2014194293 A1 | 12/2014 |
| WO | 2015013388 A2 | 1/2015 |
| WO | 2015033172 A1 | 3/2015 |
| WO | 2015033173 A1 | 3/2015 |
| WO | 2015036499 A1 | 3/2015 |
| WO | 2015038538 A1 | 3/2015 |
| WO | WO2015061668 A1 * | 4/2015 |
| WO | 2015088930 A1 | 6/2015 |
| WO | 2015124703 A1 | 8/2015 |
| WO | 2015181342 A1 | 12/2015 |

OTHER PUBLICATIONS

Padlan, Advances in Protein Chemistry, 1996, 49:57-133.*
Tzartos et al., Methods in Molecular Biology, 1996, 66:55-66.*
Paul, Fundamental Immunology, 3rd Edition, 1993, pp. 292-295.*
Rudikoff et al., Proc. Natl. Acad. Sci. USA, 79(6):1979-1983, Mar. 1982.*
Colman, Research in Immunology, 145:33-36, 1994.*
Bendig, Methods: A Companion to Methods in Enzymology, 1995; 8:83-93.*
Berglund et al, Protein Science, 2008, 17:606-613.*
Carter et al., "PD-1:PD-L inhibitory pathway affects both CD4 and CD8 T cells and is overcome by IL-2", Eur J Immunol, 2002, vol. 32, pp. 634-643.
Entrez Gene ID: 29126, CD274 CD274 molecule [*Homo sapiens* (human)], http://www.ncbi.nlm.nih.gov/gene/29126, last updated May 4, 2015.
Freeman et al., "Engagement of PD-1 Immunoinhibitory Receptor by a Novel B7 Family Member Leads to Negative Regulation of Lymphocyte Activation", J Exp Med. vol. 192, No. 7, Oct. 2, 2000, pp. 1027-1034.

(Continued)

*Primary Examiner* — Hong Sang
(74) *Attorney, Agent, or Firm* — Ventana Medical Systems, Inc.

(57) ABSTRACT

Provided herein are PD-L1 antibodies and methods for using the same for diagnosing a medical condition associated with elevated PD-L1 levels (e.g., cancer) in subjects in need thereof and antigen binding fragments thereof. The PD-L1 antibodies and antigen binding fragments are also useful in evaluating the efficacy of a particular therapeutic regime in a subject diagnosed as having a PD-L1-related medical condition.

12 Claims, 10 Drawing Sheets
(8 of 10 Drawing Sheet(s) Filed in Color)

(56) References Cited

OTHER PUBLICATIONS

National Cancer Institute: NCI Drug Dictionary. Definition of pembrolizumab. http://www.cancer.gov/drugdictionary?cdrid=695789, downloaded May 2, 2017.
CellSignal.com, Cancer Immunology, http://www.cellsignal.com/contents/science-cancer-research/pivotal-tumor-immunology-targets-pd-l1/pd-li-signaling, downloaded May 2, 2017.
Gibney, Michael, "Merck Serono Initiates Phse II Study of Anti-PD-L1 Antibody MSB0010718C in Metastatic Merkel Cell Carcinoma", Fierce Biotech Drug Development Forum, Jul. 29, 2014, pp. 1-3, http://www.fiercebiotech.com/press-releases/merck-serono-initiates-phase-ii-study-anti-pd-l1-antibody-msb0010718c-metas.
ClinicalTrials.gov, pp. 1-3, https://clinicaltrials.gov/ct2/show/NCT02125461?term=medi4736+nsclc&rank=3, last updated May 1, 2017.
Latchman et al., "PD-L2 is a second ligand for PD-1 and inhibits T cell activation", Nat Immunol., 2001, vol. 2, pp. 261-268.
Ohigashi et al., "Clinical Significance of Programmed Death-1 Ligand-1 and Programmed Death- Ligand-2 Expression in Human Esophageal Cancer," Clin Cancer Res, Apr. 15, 20015, vol. 11, pp. 2947-2953.
UniProtKB: Q9NZQ7—PD1L1_Human UniProt, Programmed cell death 1 ligand1, CD274, http://www.uniprot.org/uniprot/Q9NZQ7, downloaded May 21, 2015.
Genentech Press Release, "Investigational Immunotherapy Anti-PDL1 (MPDL3280A) Shrank Tumors in 43 Percent of People With a Specific Type of Metastic Bladder Cancer in a Genentech Study", May 31, 2014, pp. 1-6, www.gene.com/media/press-releases/14566/2014-05-31/investigational-immunotherapy-anti-pdl1-.
Velcheti et al., "Programmed death ligand-1 expression in non-small cell lung cancer", Laboratory Investigation, vol. 94, Nov. 11, 2013, pp. 107-116.
Cellsignal.com, PD-L1 (E1L3N®) XP® Rabbit mAb #13684, pp. 1-12, http://www.cellsignal.com/products/primary-antibodies/13684?id=proteomics&utm_source=Sales+Flyer&utm_medium=offline&utm_campaign=NPI&utm_content=PDL1, downloaded May 2, 2017.
AbD serotec, Catalogue d'anticorps 2011, pp. 1 and 140, www.abdserotec.com/france.
McLaughlin, et al., "Domain-specific PD-L1 protein measurement in non-small cell lung cancer (NSCLC)", Journal of Clinical Oncology, 2014, vol. 32, No. 15 Supplement (May 20 Supplement), pp. 8064, abstract.
International Search Report mailed Jul. 30, 2015 for corresponding PCT Application No. PCT/EP2015/061921 filed May 29, 2015.
Afanasiev et al, 2013, "Merkel Polyomavirus-Specific T Cells Fluctuate with Merkel Cell Carcinoma Burden and Express Therapeutically Targetable PD-1 and Tim-3 Exhaustion Markers", Clinical Cancer Research, 19 (19):5351-5360.
Ali et al, 2015, "PD-L1 protein expression in breast cancer is rare, enriched in basal-like tumours and associated with infiltrating lymphocytes", Annals of Oncology, 26:1488-1493.
Almagro et al, 2008, "Humanization of Antibodies, Frontiers in Bioscience", 13:1619-1633.
Anonymous, Dual IHC on Discovery Ultra Research Instrument, Ventana Research Protocols, Jan. 1, 2014, URL: http://www.ventana.com/researchprotocols, XP055337858.
Anonymous, Dual IHC on Discovery Ultra Research Instrument, Ventana Research Protocols, Jan. 1, 2014, URL: http://www.ventana.com/researchprotocols, XP055337860.
Brahmer et al, 2012, "Safety and Activity of Anti-PD-L1 Antibody in Patients with Advanced Cancer", The New England Journal of Medicine, 366(26):2455-2465.
Brown et al, 2003, "Blockade of Programmed Death-1 Ligands on Dendritic Cells Enhances T Cell Activation and Oytokine Production", The Journal of Immunology, 170:1257-1266.
Brown, McKay et al., 1996, "Tolerance to Single, But Not Multiple, Amino Acid Replacements in Antibody VH CDR2 A Means of Minimizing B Cell Wastage from Somatic Hypermutation?", The Journal of Immunology, 156:3285-3291.

Butte et al, 2007, "Programmed Death-1 Ligand 1 Interacts Specifically with the B7-1 Costimulatory Molecule to Inhibit T Cell Responses", Immunity, 27:111-122.
Calles et al, 2014, "Differential expression of LKB1, PD-L1, and PD-L2 in KRAS-mutant non-small cell lung cancer in never-smokers", Journal of Clinical Oncology, 32(15):8032.
Chakravarti et al, 2015, "Predictive factors of activity of anti-programmed death-1/ programmed death ligand-1 drugs: immunohistochemistry analysis", Translational Lung Cancer Research, 4:743-751.
Chen et al, 2012, "Molecular Pathways: Next-Generation Immunotherapy-Inhibiting Programmed Death-Ligand 1 and Programmed Death-1", Clinical Cancer Research, 18(24):6580-6587.
Chen et al, 2013, "PD-L1 Expression Is Characteristic of a Subset of Aggressive B-cell Lymphomas and Virus-Associated Malignancies, Clinical Cancer Research", 19(13):3462-3473.
Cheong et al, 1996, "Unexpected Epithelial Membrane Antigen (EMA) and Cytokeratin Expression in a Case of Infantile Acute Monoblastic Leukaemia", Hematology, 1:223-225.
Choueiri et al, 2014, "Correlation of PD-L1 Tumor Expression and Treatment Outcomes in Patients with Renal sell Carcinoma Receiving Sunitinib or Pazopanib: Results from COMPARZ, a Randomized Controlled Trial", Clinical cancer Research, 21(5):1071-1077.
Corada et al, 2001, "Monoclonal antibodies directed to different regions of vascular endothelial cadherin extracellular domain affect adhesion and clustering of the protein and modulate endothelial permeability", Blood, 97(6):1679-1684.
De Genst et al, 2006, "Antibody repertoire development in camelids", Developmental and Comparative Immunology, 30:187-198.
Dong et al, 2002, "Tumor-associated B7-H1 promotes T-cell apoptosis: A potential mechanism of immune evasion", Nature Medicine, 8(8):793-800.
Gaiser et al, 2007, "Tyramide Signal Amplification: An Enhanced Method for Immunohistochemistry on Methyl-Methacrylate-Embedded Bone Marrow Trephine Sections", Acta Haematology, 117:122-127.
Ghebeh et al, 2006, "The B7-H1 (PD-L1) T Lymphocyte—Inhibitory Molecule Is Expressed in Breast Cancer Patients with Infiltrating Ductal Carcinoma: Correlation with Important High-Risk Prognostic Factors", Neoplasia, 8(3):190-198.
Ghebeh et al, 2008, "FOXP3+ Tregs and B7-H1+/PD-1+ T lymphocytes co-infiltrate the tumor tissues of high-risk breast cancer patients: Implication for immunotherapy", BMC Cancer, 8:57.
Gustmann et al, 1991, "Cytokeratin Expression and Vimentin Content in Large Cell Anaplastic Lymphomas and Other Non-Hodgkin's Lymphomas", American Journal of Pathology, 138(6):1413-1422.
Hamanishi et al, 2007, "Programmed cell death 1 ligand 1 and tumor-infiltrating CD8+ T lymphocytes are prognostic factors of human ovarian cancer", PNAS, 104(9):3360-3365.
Hamid et al, 2013, "Anti-programmed death-1 and anti-programmed death-ligand 1 antibodies in cancer therapy", Expert Opinion on Biological Therapy, 13(6):847-861.
Iwai et al, 2002, "Involvement of PD-L1 on tumor cells in the escape from host immune system and tumor immunotherapy by PD-L1 blockade", PNAS, 99(19):12293-12297.
Kwak et al, 1996, "A convenient method for epitope competition analysis of two monoclonal antibodies for their antigen binding", Journal of Immunological Methods, 191:49-54.
Mu et al, 2011, "High expression of PD-L1 in lung cancer may contribute to poor prognosis and tumor cells immune ascape through suppressing tumor infiltrating dendritic cells maturation", Medical Oncology, 28:682-688.
Mullane et al, 2014, "PD-L1 expression in mononuclear cells and not in tumor cells, correlated with prognosis in metastatic urothelial carcinoma", Journal of Clinical Oncology, 32(15):4552.
Ogata et al, 2012, "Differences in blast immunophenotypes among disease types in myelodysplastic syndromes: A multicenter validation study", Leukemia Research, 36:1229-1236.

(56) References Cited

OTHER PUBLICATIONS

Powderly et al, 2013, "Biomarkers and Associations With the Clinical Activity of PD-L1 Blockade in a MPDL3280A Study", ASCO Presentation, slides 9-14.
Ribas et al, 2014, "The Future of Cancer Therapy: Selecting Patients Likely to Respond to PD1/L1 Blockade", Clinical Cancer Research, 20:4982-4984.
Shen et al, "Impaired ICOSL in human myeloid dendritic cells promotes Th2 responses in patients with allergic rhinitis and asthma", Clinical & Experimental Allergy, 44(6):831-841. 2014.
Sznol et al, 2013, "Antagonist Antibodies to PD-1 and B7-H1 (PD-L1) in the Treatment of Advanced Human Cancer", Clinical Cancer Research, 19(5):1021-1034.
Taube et al, 2012, "Colocalization of Inflammatory Response with B7-H1 Expression in Human Melanocytic Lesions Supports an Adaptive Resistance Mechanism of Immune Escape", Science Translational Medicine, 4(127):127ra37.
Topalian et al, 2012, "Safety, Activity, and Immune Correlates of Anti-PD-1 Antibody in Cancer", The New England Journal of Medicine, 366(26):2443-2454.
Tumeh et al, 2014, "PD-1 blockade induces responses by inhibiting adaptive immune resistance", Nature, 515(7528):568-571.
Ventana Medical Systems, Inc., 3-25. Ventana Medical Systems, Inc. and MedImmune collaborate to develop a custom PD-L1 Assay for immunotherapy clinical trials, 2014, 2 pages.
Warford et al, 2014, "Antigen retrieval, blocking, detection and visualisation systems in immunohistochemistry: A review and practical evaluation of tyramide and rolling circle amplification systems", Methods, 70:28-33.
Weber et al, 2013, "Safety, Efficacy, and Biomarkers of Nivolumab With Vaccine in Ipilimumab-Refractory or -Naive Melanoma", Journal of Clinical Oncology, 31:4311-4318.
Xu et al, 2014, "Loss of Lkb1 and Pten Leads to Lung Squamous Cell Carcinoma with Elevated PD-L1 Expression", Cancer Cell, 25:590-604.
Yunmei et al, 2014, "VSIG4 expression on macrophages facilitates lung cancer development", Laboratory Investigation, 94:709-710.
Zhang et al, 2009, "PD-1/PD-L1 interactions inhibit antitumor immune responses in a murine acute myeloid eukemia model", Blood, 114(8):1545-1552.

\* cited by examiner

000

SEQUENCE LISTING

```
<160> NUMBER OF SEQ ID NOS: 35

<210> SEQ ID NO 1
<211> LENGTH: 19
<212> TYPE: PRT
<213> ORGANISM: Artificial Sequence
<220> FEATURE:
<223> OTHER INFORMATION: Fragment of human PDL1

<400> SEQUENCE: 1

Cys Gly Ile Gln Asp Thr Asn Ser Lys Lys Gln Ser Asp Thr His Leu
1               5                   10                  15
```

Glu Glu Thr

```
<210> SEQ ID NO 2
<211> LENGTH: 114
<212> TYPE: PRT
<213> ORGANISM: Artificial Sequence
<220> FEATURE:
<223> OTHER INFORMATION: SP263 HC immunoglobulin variable domain
      sequence

<400> SEQUENCE: 2
```

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Asn His Ala
            20                  25                  30

Ile Ser Trp Val Arg Gln Ala Pro Gly Lys Gly Leu Glu Trp Ile Gly
        35                  40                  45

Thr Ile Asn Ser Asp Thr His Thr Tyr Tyr Ala Thr Trp Pro Lys Gly
    50                  55                  60

Arg Phe Thr Ile Ser Lys Thr Ser Ser Thr Thr Val Asp Leu Lys Met
65                  70                  75                  80

Thr Ser Pro Thr Thr Glu Asp Thr Ala Thr Tyr Phe Cys Ala Arg Arg
                85                  90                  95

Ile Phe Ser Ser Ser Asn Ile Trp Gly Pro Gly Thr Leu Val Thr Val
            100                 105                 110

Ser Ser

```
<210> SEQ ID NO 3
<211> LENGTH: 112
<212> TYPE: PRT
<213> ORGANISM: Artificial Sequence
<220> FEATURE:
<223> OTHER INFORMATION: SP263 LC immunoglobulin variable domain
      sequence (kappa)

<400> SEQUENCE: 3
```

Ala Ile Val Met Thr Gln Thr Ser Ser Pro Val Ser Ala Val Val Gly
1               5                   10                  15

Gly Thr Val Ala Ile Asn Cys Gln Ala Ser Gln Ser Ile Tyr Asn Asn
            20                  25                  30

Asn Trp Leu Ser Trp Phe Gln Gln Lys Pro Gly Gln Pro Pro Lys Leu
        35                  40                  45

Leu Ile Tyr Leu Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Val
65                  70                  75                  80

Val Cys Asp Asp Ala Ala Thr Tyr Tyr Cys Ile Gly Gly Glu Ser Ser
                85                  90                  95

Asn Asn Asp Gly Ile Ala Phe Gly Gly Gly Thr Glu Val Val Val Lys
            100                 105                 110

```
<210> SEQ ID NO 4
<211> LENGTH: 113
<212> TYPE: PRT
<213> ORGANISM: Artificial Sequence
<220> FEATURE:
<223> OTHER INFORMATION: J45H2L4 HC immunoglobulin variable domain
      sequence

<400> SEQUENCE: 4
```

```
Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Asn Ala
            20                  25                  30

Ile Ser Trp Val Arg Gln Ala Pro Gly Lys Gly Leu Glu Trp Ile Gly
            35                  40                  45

Thr Ile Asn Ser Asp Ser His Ile Tyr Ser Ala Thr Trp Ala Lys Gly
        50                  55                  60

Arg Phe Thr Ile Ser Lys Thr Ser Thr Ala Val Asp Leu Lys Met Thr
65                  70                  75                  80

Ser Pro Thr Thr Glu Asp Thr Ala Thr Tyr Phe Cys Ala Gly Arg Leu
                85                  90                  95

Phe Ser Ser Thr Asn Ile Trp Gly Pro Gly Thr Leu Val Thr Val Ser
            100                 105                 110

Ser
```

<210> SEQ ID NO 5
<211> LENGTH: 110
<212> TYPE: PRT
<213> ORGANISM: Artificial Sequence
<220> FEATURE:
<223> OTHER INFORMATION: J45H2L4 LC immunoglobulin variable domain
      sequence (kappa)

<400> SEQUENCE: 5

```
Val Met Thr Gln Thr Ser Ser Pro Val Ser Ala Ala Val Gly Gly Thr
1               5                   10                  15

Val Thr Ile Asn Cys Gln Ala Ser Gln Ser Ile Tyr Lys Asp Asn Trp
            20                  25                  30

Leu Ser Trp Phe Gln Gln Lys Pro Gly Gln Pro Pro Lys Leu Leu Ile
            35                  40                  45

Tyr Leu Ala Ser Thr Leu Ala Ser Gly Val Pro Ser Arg Phe Lys Gly
        50                  55                  60

Ser Gly Ser Gly Thr Gln Phe Thr Leu Thr Ile Ser Asp Val Val Cys
65                  70                  75                  80

Asp Asp Ala Ala Thr Tyr Tyr Cys Leu Gly Gly Glu Ser Ser Ser Asp
                85                  90                  95

Asp Gly Ile Ala Phe Gly Gly Gly Thr Glu Val Val Val Lys
            100                 105                 110
```

<210> SEQ ID NO 6
<211> LENGTH: 113
<212> TYPE: PRT
<213> ORGANISM: Artificial Sequence
<220> FEATURE:
<223> OTHER INFORMATION: J27H6L4 HC immunoglobulin variable domain
      sequence

<400> SEQUENCE: 6

```
Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser His Ala
            20                  25                  30

Ile Ser Trp Val Arg Gln Ala Pro Gly Lys Gly Leu Glu Trp Ile Gly
            35                  40                  45

Thr Ile Asn Ser Asp Ser His Thr Tyr Tyr Ala Thr Trp Ala Lys Gly
        50                  55                  60

Arg Phe Thr Ser Ser Lys Thr Ser Thr Thr Val Asp Leu Lys Leu Thr
```

```
                65                  70                  75                  80
Ser Pro Thr Thr Glu Asp Thr Ala Thr Tyr Phe Cys Ala Arg Arg Ile
                    85                  90                  95

Phe Ser Ser Ser Asn Ile Trp Gly Pro Gly Thr Leu Val Thr Val Ser
                100                 105                 110

Ser

<210> SEQ ID NO 7
<211> LENGTH: 110
<212> TYPE: PRT
<213> ORGANISM: Artificial Sequence
<220> FEATURE:
<223> OTHER INFORMATION: J27H6L4 LC immunoglobulin variable domain
      sequence (kappa)

<400> SEQUENCE: 7

Val Met Thr Gln Thr Ser Ser Pro Val Ser Ala Ala Val Gly Gly Thr
1               5                   10                  15

Val Thr Ile Asn Cys Gln Ala Ser Gln Ser Ile Tyr Asn Asn Asn Trp
                20                  25                  30

Leu Ser Trp Phe Gln Gln Lys Pro Gly Gln Pro Pro Lys Leu Leu Ile
            35                  40                  45

Tyr Leu Ala Ser Thr Leu Ala Ser Gly Val Pro Ser Arg Phe Lys Gly
        50                  55                  60

Ser Gly Ser Gly Thr Gln Ser Thr Leu Thr Ile Ser Asp Val Val Cys
65                  70                  75                  80

Asp Asp Ala Ala Thr Tyr Tyr Cys Ile Gly Gly Glu Ser Ser Asn Thr
                85                  90                  95

Asp Gly Ile Ala Phe Gly Gly Gly Thr Glu Val Val Val Glu
                100                 105                 110

<210> SEQ ID NO 8
<211> LENGTH: 5
<212> TYPE: PRT
<213> ORGANISM: Artificial Sequence
<220> FEATURE:
<223> OTHER INFORMATION: CDR1 consensus sequence
<220> FEATURE:
<221> NAME/KEY: X
<222> LOCATION: (1)..(1)
<223> OTHER INFORMATION: N or S
<220> FEATURE:
<221> NAME/KEY: X
<222> LOCATION: (2)..(2)
<223> OTHER INFORMATION: H or N

<400> SEQUENCE: 8

Xaa Xaa Ala Ile Ser
1               5

<210> SEQ ID NO 9
<211> LENGTH: 16
<212> TYPE: PRT
<213> ORGANISM: Artificial Sequence
<220> FEATURE:
<223> OTHER INFORMATION: Heavy chain CDR2 consensus sequence
<220> FEATURE:
<221> NAME/KEY: X
<222> LOCATION: (6)..(6)
<223> OTHER INFORMATION: T or S
<220> FEATURE:
<221> NAME/KEY: X
<222> LOCATION: (8)..(8)
<223> OTHER INFORMATION: T or I
<220> FEATURE:
```

```
<221> NAME/KEY: X
<222> LOCATION: (10)..(10)
<223> OTHER INFORMATION: Y or S
<220> FEATURE:
<221> NAME/KEY: X
<222> LOCATION: (14)..(14)
<223> OTHER INFORMATION: P or A

<400> SEQUENCE: 9

Thr Ile Asn Ser Asp Xaa His Xaa Tyr Xaa Ala Thr Trp Xaa Lys Gly
1               5                   10                  15

<210> SEQ ID NO 10
<211> LENGTH: 8
<212> TYPE: PRT
<213> ORGANISM: Artificial Sequence
<220> FEATURE:
<223> OTHER INFORMATION: Heavy chain CDR3 consensus sequence
<220> FEATURE:
<221> NAME/KEY: X
<222> LOCATION: (2)..(2)
<223> OTHER INFORMATION: I or L
<220> FEATURE:
<221> NAME/KEY: X
<222> LOCATION: (6)..(6)
<223> OTHER INFORMATION: S or T

<400> SEQUENCE: 10

Arg Xaa Phe Ser Ser Xaa Asn Ile
1               5

<210> SEQ ID NO 11
<211> LENGTH: 13
<212> TYPE: PRT
<213> ORGANISM: Artificial Sequence
<220> FEATURE:
<223> OTHER INFORMATION: Light chain CDR1 consensus sequence
<220> FEATURE:
<221> NAME/KEY: X
<222> LOCATION: (8)..(8)
<223> OTHER INFORMATION: N or K
<220> FEATURE:
<221> NAME/KEY: X
<222> LOCATION: (9)..(9)
<223> OTHER INFORMATION: N or D

<400> SEQUENCE: 11

Gln Ala Ser Gln Ser Ile Tyr Xaa Xaa Asn Trp Leu Ser
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Light chain CDR2

<400> SEQUENCE: 12

Leu Ala Ser Thr Leu Ala Ser
1               5

<210> SEQ ID NO 13
<211> LENGTH: 12
<212> TYPE: PRT
<213> ORGANISM: Artificial Sequence
<220> FEATURE:
<223> OTHER INFORMATION: Light chain CDR3 consensus sequence
<220> FEATURE:
<221> NAME/KEY: X
<222> LOCATION: (1)..(1)
<223> OTHER INFORMATION: L or I
```

```
<220> FEATURE:
<221> NAME/KEY: X
<222> LOCATION: (7)..(7)
<223> OTHER INFORMATION: N or S
<220> FEATURE:
<221> NAME/KEY: X
<222> LOCATION: (8)..(8)
<223> OTHER INFORMATION: N, T or D

<400> SEQUENCE: 13

Xaa Gly Gly Glu Ser Ser Xaa Xaa Asp Gly Ile Ala
1               5                   10

<210> SEQ ID NO 14
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 14

Asn His Ala Ile Ser
1               5

<210> SEQ ID NO 15
<211> LENGTH: 16
<212> TYPE: PRT
<213> ORGANISM: Artificial Sequence
<220> FEATURE:
<223> OTHER INFORMATION: Heavy chain CDR2

<400> SEQUENCE: 15

Thr Ile Asn Ser Asp Thr His Thr Tyr Tyr Ala Thr Trp Pro Lys Gly
1               5                   10                  15

<210> SEQ ID NO 16
<211> LENGTH: 8
<212> TYPE: PRT
<213> ORGANISM: Artificial Sequence
<220> FEATURE:
<223> OTHER INFORMATION: Heavy chain CDR3

<400> SEQUENCE: 16

Arg Ile Phe Ser Ser Ser Asn Ile
1               5

<210> SEQ ID NO 17
<211> LENGTH: 13
<212> TYPE: PRT
<213> ORGANISM: Artificial Sequence
<220> FEATURE:
<223> OTHER INFORMATION: Light chain CDR1

<400> SEQUENCE: 17

Gln Ala Ser Gln Ser Ile Tyr Asn Asn Asn Trp Leu Ser
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Light chain CDR3

<400> SEQUENCE: 18

Ile Gly Gly Glu Ser Ser Asn Asn Asp Gly Ile Ala
1               5                   10
```

```
<210> SEQ ID NO 19
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 19

Ser Asn Ala Ile Ser
1               5

<210> SEQ ID NO 20
<211> LENGTH: 16
<212> TYPE: PRT
<213> ORGANISM: Artificial Sequence
<220> FEATURE:
<223> OTHER INFORMATION: Heavy chain CDR2

<400> SEQUENCE: 20

Thr Ile Asn Ser Asp Ser His Ile Tyr Ser Ala Thr Trp Ala Lys Gly
1               5                   10                  15

<210> SEQ ID NO 21
<211> LENGTH: 8
<212> TYPE: PRT
<213> ORGANISM: Artificial Sequence
<220> FEATURE:
<223> OTHER INFORMATION: Heavy chain CDR3

<400> SEQUENCE: 21

Arg Leu Phe Ser Ser Thr Asn Ile
1               5

<210> SEQ ID NO 22
<211> LENGTH: 13
<212> TYPE: PRT
<213> ORGANISM: Artificial Sequence
<220> FEATURE:
<223> OTHER INFORMATION: Light chain CDR1

<400> SEQUENCE: 22

Gln Ala Ser Gln Ser Ile Tyr Lys Asp Asn Trp Leu Ser
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Light chain CDR3

<400> SEQUENCE: 23

Leu Gly Gly Glu Ser Ser Ser Asp Asp Gly Ile Ala
1               5                   10

<210> SEQ ID NO 24
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 24

Ser His Ala Ile Ser
1               5
```

-continued

```
<210> SEQ ID NO 25
<211> LENGTH: 16
<212> TYPE: PRT
<213> ORGANISM: Artificial Sequence
<220> FEATURE:
<223> OTHER INFORMATION: Heavy chain CDR2

<400> SEQUENCE: 25

Thr Ile Asn Ser Asp Ser His Thr Tyr Tyr Ala Thr Trp Ala Lys Gly
1               5                   10                  15

<210> SEQ ID NO 26
<211> LENGTH: 12
<212> TYPE: PRT
<213> ORGANISM: Artificial Sequence
<220> FEATURE:
<223> OTHER INFORMATION: Light chain CDR3

<400> SEQUENCE: 26

Ile Gly Gly Glu Ser Ser Asn Thr Asp Gly Ile Ala
1               5                   10

<210> SEQ ID NO 27
<211> LENGTH: 384
<212> TYPE: PRT
<213> ORGANISM: Homo sapiens

<400> SEQUENCE: 27

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
            20                  25                  30

Tyr His Pro Thr Ser Val Thr Val Thr Trp Tyr Met Gly Thr Gln Ser
        35                  40                  45

Gln Pro Gln Arg Thr Phe Pro Glu Ile Gln Arg Arg Asp Ser Tyr Tyr
    50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro Glu Ser Pro Lys Ala Gln Ala Ser Ser Val Pro
            100                 105                 110

Thr Ala Gln Pro Gln Ala Glu Gly Ser Leu Ala Lys Ala Thr Thr Ala
        115                 120                 125

Pro Ala Thr Thr Arg Asn Thr Gly Arg Gly Gly Glu Glu Lys Lys Lys
    130                 135                 140

Glu Lys Glu Lys Glu Glu Gln Glu Glu Arg Glu Thr Lys Thr Pro Glu
145                 150                 155                 160

Cys Pro Ser His Thr Gln Pro Leu Gly Val Tyr Leu Leu Thr Pro Ala
                165                 170                 175

Val Gln Asp Leu Trp Leu Arg Asp Lys Ala Thr Phe Thr Cys Phe Val
            180                 185                 190

Val Gly Ser Asp Leu Lys Asp Ala His Leu Thr Trp Glu Val Ala Gly
        195                 200                 205

Lys Val Pro Thr Gly Gly Val Glu Glu Gly Leu Leu Glu Arg His Ser
    210                 215                 220

Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
```

```
                    245                 250                 255
Pro Pro Gln Arg Leu Met Ala Leu Arg Glu Pro Ala Gln Ala Pro
            260                 265                 270

Val Lys Leu Ser Leu Asn Leu Leu Ala Ser Ser Asp Pro Glu Ala
            275                 280                 285

Ala Ser Trp Leu Leu Cys Glu Val Ser Gly Phe Ser Pro Pro Asn Ile
            290                 295                 300

Leu Leu Met Trp Leu Glu Asp Gln Arg Glu Val Asn Thr Ser Gly Phe
305                 310                 315                 320

Ala Pro Ala Arg Pro Pro Gln Pro Gly Ser Thr Thr Phe Trp Ala
            325                 330                 335

Trp Ser Val Leu Arg Val Pro Ala Pro Pro Ser Pro Gln Pro Ala Thr
                340                 345                 350

Tyr Thr Cys Val Val Ser His Glu Asp Ser Arg Thr Leu Leu Asn Ala
            355                 360                 365

Ser Arg Ser Leu Glu Val Ser Tyr Val Thr Asp His Gly Pro Met Lys
370                 375                 380
```

<210> SEQ ID NO 28
<211> LENGTH: 330
<212> TYPE: PRT
<213> ORGANISM: Homo sapiens

<400> SEQUENCE: 28

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240
```

```
Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 29
<211> LENGTH: 326
<212> TYPE: PRT
<213> ORGANISM: Homo sapiens

<400> SEQUENCE: 29

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285
```

```
Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 30
<211> LENGTH: 377
<212> TYPE: PRT
<213> ORGANISM: Homo sapiens

<400> SEQUENCE: 30

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
```

```
            325                 330                 335
Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro Gly Lys
            370                 375
```

<210> SEQ ID NO 31
<211> LENGTH: 452
<212> TYPE: PRT
<213> ORGANISM: Homo sapiens

<400> SEQUENCE: 31

```
Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Leu Ser Trp Lys Tyr Lys Asn Asn Ser
            35                  40                  45

Asp Ile Ser Ser Thr Arg Gly Phe Pro Ser Val Leu Arg Gly Gly Lys
50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
            85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
            115                 120                 125

Lys Ser Lys Leu Ile Cys Gln Ala Thr Gly Phe Ser Pro Arg Gln Ile
130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
            165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
            195                 200                 205

Asn Ala Ser Ser Met Cys Val Pro Asp Gln Asp Thr Ala Ile Arg Val
            210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
            245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
            275                 280                 285

Ser Ile Cys Glu Asp Asp Trp Asn Ser Gly Glu Arg Phe Thr Cys Thr
            290                 295                 300

Val Thr His Thr Asp Leu Pro Ser Pro Leu Lys Gln Thr Ile Ser Arg
305                 310                 315                 320
```

```
Pro Lys Gly Val Ala Leu His Arg Pro Asp Val Tyr Leu Leu Pro Pro
            325                 330                 335
Ala Arg Glu Gln Leu Asn Leu Arg Glu Ser Ala Thr Ile Thr Cys Leu
        340                 345                 350
Val Thr Gly Phe Ser Pro Ala Asp Val Phe Val Gln Trp Met Gln Arg
            355                 360                 365
Gly Gln Pro Leu Ser Pro Glu Lys Tyr Val Thr Ser Ala Pro Met Pro
    370                 375                 380
Glu Pro Gln Ala Pro Gly Arg Tyr Phe Ala His Ser Ile Leu Thr Val
385                 390                 395                 400
Ser Glu Glu Glu Trp Asn Thr Gly Glu Thr Tyr Thr Cys Val Ala His
                405                 410                 415
Glu Ala Leu Pro Asn Arg Val Thr Glu Arg Thr Val Asp Lys Ser Thr
            420                 425                 430
Gly Lys Pro Thr Leu Tyr Asn Val Ser Leu Val Met Ser Asp Thr Ala
        435                 440                 445
Gly Thr Cys Tyr
        450

<210> SEQ ID NO 32
<211> LENGTH: 327
<212> TYPE: PRT
<213> ORGANISM: Homo sapiens

<400> SEQUENCE: 32

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Ser Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
    210                 215                 220
Glu Pro Gln Val Tyr Thr Leu Pro Pro Ser Gln Glu Glu Met Thr Lys
225                 230                 235                 240
```

```
Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 33
<211> LENGTH: 353
<212> TYPE: PRT
<213> ORGANISM: Homo sapiens

<400> SEQUENCE: 33

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
    210                 215                 220

Thr Phe Arg Pro Glu Val His Leu Leu Pro Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
```

```
                    275                 280                 285
Thr Thr Thr Phe Ala Val Thr Ser Ile Leu Arg Val Ala Ala Glu Asp
    290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
                340                 345                 350

Tyr

<210> SEQ ID NO 34
<211> LENGTH: 340
<212> TYPE: PRT
<213> ORGANISM: Homo sapiens

<400> SEQUENCE: 34

Ala Ser Pro Thr Ser Pro Lys Val Phe Pro Leu Ser Leu Asp Ser Thr
1               5                   10                  15

Pro Gln Asp Gly Asn Val Val Val Ala Cys Leu Val Gln Gly Phe Phe
                20                  25                  30

Pro Gln Glu Pro Leu Ser Val Thr Trp Ser Glu Ser Gly Gln Asn Val
            35                  40                  45

Thr Ala Arg Asn Phe Pro Pro Ser Gln Asp Ala Ser Gly Asp Leu Tyr
        50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Pro Pro Pro Cys Cys His Pro
                100                 105                 110

Arg Leu Ser Leu His Arg Pro Ala Leu Glu Asp Leu Leu Leu Gly Ser
            115                 120                 125

Glu Ala Asn Leu Thr Cys Thr Leu Thr Gly Leu Arg Asp Ala Ser Gly
130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
        195                 200                 205

Ser Gly Asn Thr Phe Arg Pro Glu Val His Leu Leu Pro Pro Pro Ser
    210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Phe Ala Val Thr Ser Ile Leu Arg Val Ala
        275                 280                 285

Ala Glu Asp Trp Lys Lys Gly Asp Thr Phe Ser Cys Met Val Gly His
```

```
                   290                 295                 300
Glu Ala Leu Pro Leu Ala Phe Thr Gln Lys Thr Ile Asp Arg Met Ala
305                 310                 315                 320

Gly Lys Pro Thr His Val Asn Val Ser Val Val Met Ala Glu Val Asp
                325                 330                 335

Gly Thr Cys Tyr
            340

<210> SEQ ID NO 35
<211> LENGTH: 106
<212> TYPE: PRT
<213> ORGANISM: Homo sapiens

<400> SEQUENCE: 35

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

PD-L1 ANTIBODIES AND USES THEREOF

CROSS-REFERENCE TO RELATED APPLICATIONS

This disclosure claims the benefit of U.S. 62/004,572, filed May 29, 2014, and U.S. 62/069,420, filed Oct. 28, 2014, the contents of which are hereby incorporated by reference in their entirety.

BACKGROUND OF THE INVENTION

Field of the Invention

This disclosure relates to novel PD-L1 antibodies and methods for using the same for detecting PD-L1 polypeptides in a biological sample. PD-L1 antibodies also are useful to evaluate the efficacy of a particular therapeutic agent in a subject diagnosed as having a PD-L1-related medical condition.

Description of Related Art

The following description is provided to assist the understanding of the reader. None of the information provided or references cited is admitted to be prior art.

Programmed death 1 (PD-1) is a member of the CD28 family of receptors, which includes CD28, CTLA-4, ICOS, PD-1, and BTLA. The initial members of the family, CD28 and ICOS, were discovered by functional effect on augmenting T cell proliferation following the addition of monoclonal antibodies (Hutloff et al., *Nature* 397:263-266 (1999); Hansen et al. *Immunogenics* 10:247-260 (1980)). Two cell surface glycoprotein ligands for PD-1 have been identified, PD-L1 and PD-L2, and have been shown to downregulate T cell activation and cytokine secretion upon binding to PD-1 (Freeman et al., *J Exp Med* 192:1027-34 (2000); Latchman et al., *Nat Immunol* 2:261-8 (2001); Carter et al., *Eur J Immunol* 32:634-43 (2002); Ohigashi et al., *Clin Cancer Res* 11:2947-53 (2005)). Both PD-L1 (B7-H1) and PD-L2 (B7-DC) are B7 homologs that bind to PD-1, but do not bind to other CD28 family members.

Human PD-L1 encodes a 290 amino acid (aa) type I membrane precursor protein with a putative 18 aa signal peptide, a 221 aa extracellular domain, a 21 aa transmembrane region, and a 31 aa cytoplasmic domain. Human PD-L1 is constitutively expressed in several organs such as heart, skeletal muscle, placenta and lung, and in lower amounts in thymus, spleen, kidney and liver. PD-L1 expression is upregulated in a small fraction of activated T and B cells and a much larger fraction of activated monocytes. PD-L1 expression is also induced in dendritic cells and keratinocytes after IFN gamma stimulation.

The PD-L1-PD1 pathway is involved in the negative regulation of some immune responses and may play an important role in the regulation of peripheral tolerance. Interaction of PD-L1 with PD1 results in inhibition of TCR-mediated proliferation and cytokine production. PD-L1 has been suggested to play a role in tumor immunity by increasing apoptosis of antigen-specific T-cell clones (Dong et al. *Nat Med* 8:793-800 (2002)). Indeed, PD-L1 expression has been found in several murine and human cancers, including human lung, ovarian and colon carcinoma and various myelomas (Iwai et al. *PNAS* 99:12293-7 (2002); Ohigashi et al. *Clin Cancer Res* 11:2947-53 (2005)). Thus, measuring the amount of PD-L1 protein in biological samples may aid in the early detection of cancer pathologies and may help assess the efficacy and durability of investigational drugs that inhibit the binding of the PD-L1 protein.

However, the use of PD-L1 protein expression as an accurate predictor for cancer and/or the efficacy of anti-PD-1 and anti-PD-L1 directed therapies remains challenging. Many commercially available antibodies directed to PD-L1 cross-react with other proteins and/or exhibit non-specific histological staining, thereby making them unreliable diagnostic reagents. Furthermore, conflicting results have been observed when comparing PD-L1 antibodies targeting the extracellular domain versus the intracellular domain. McLaughlin et al., *J. Clin Oncol* 32:5 (2014). Moreover, the evaluation of PD-L1 expression in non-small cell lung cancer samples using commercially available antibodies such as E1L3N® (Cell Signaling Technology, MA), 5H1 (Dong et al., *Nat Med.* 8:793-800 (2002)) and E1J2J, yielded discordant results. McLaughlin et al., *J. Clin Oncol* 32:5 (2014).

SUMMARY OF THE INVENTION

Provided herein is an isolated antibody comprising a heavy chain (HC) immunoglobulin variable domain sequence and a light chain (LC) immunoglobulin variable domain sequence, wherein the antibody binds to an epitope of human PD-L1 comprising the amino acid sequence CGIQDTNSKKQSDTHLEET (SEQ ID NO: 1) and/or wherein the antibody binding the epitope of human PD-L1 has a half maximal effective concentration ($EC_{50}$) of at least $1.5 \times 10^{-11}$ M.

In a further aspect, (a) the HC of the isolated antibody comprises a CDR3 consensus sequence $RX_1FSSX_2NI$ (SEQ ID NO: 10), wherein $X_1$ is I or L, and $X_2$ is S or T; and/or (b) the LC of the isolated antibody comprises a CDR3 consensus sequence $X_3GGESSX_4X_5DGIA$ (SEQ ID NO: 13), wherein $X_3$ is L or I, $X_4$ is N or S, and $X_5$ is N, T or D; and/or (c) the HC of the isolated antibody comprises a CDR3 consensus sequence $RX_1FSSX_2NI$ (SEQ ID NO: 10), wherein $X_1$ is I or L, and $X_2$ is S or T, and wherein the LC of the isolated antibody comprises a CDR3 consensus sequence $X_3GGESSX_4X_5DGIA$ (SEQ ID NO: 13), wherein $X_3$ is L or I, $X_4$ is N or S, and $X_5$ is N, T or D.

Additionally or alternatively, in some aspects of the antibody, the HC further comprises a CDR2 consensus sequence $TINSDX_6HX_7YX_8ATWX_9KG$ (SEQ ID NO: 9), wherein $X_6$ is T or S, $X_7$ is T or I, $X_8$ is Y or S, and $X_9$ is P or A.

Additionally or alternatively, in some aspects of the antibody, the HC further comprises a CDR1 consensus sequence $X_{10}X_{11}AIS$ (SEQ ID NO: 8), wherein $X_{10}$ is N or S, and $X_{11}$ is H or N.

Additionally or alternatively, in some aspects of the antibody, the LC further comprises a CDR2 sequence LASTLAS (SEQ ID NO: 12).

Additionally or alternatively, in some aspects of the antibody, the LC further comprises a CDR1 consensus sequence $QASQSIYX_{12}X_{13}NWLS$ (SEQ ID NO: 11), wherein $X_{12}$ is N or K and $X_{13}$ is N or D.

In some aspects of the antibody, the HC comprises (a) a HC CDR1 comprising the amino acid sequence NHAIS (SEQ ID NO: 14); and/or (b) a HC CDR2 comprising the amino acid sequence TINSDTHTYYATWPKG (SEQ ID NO: 15); and/or (c) a HC CDR3 comprising the amino acid sequence RIFSSSNI (SEQ ID NO: 16); and/or the LC comprises (a) a LC CDR1 comprising the amino acid sequence QASQSIYNNNWLS (SEQ ID NO: 17); and/or (b) a LC CDR2 comprising the amino acid sequence LASTLAS (SEQ ID NO: 12); and/or (c) a LC CDR3 comprising the amino acid sequence IGGESSNNDGIA (SEQ ID NO: 18).

In some aspects of the antibody, the HC comprises (a) a HC CDR1 comprising the amino acid sequence SNAIS (SEQ ID NO: 19); and/or (b) a HC CDR2 comprising the amino acid sequence TINSDSIHYSATWAKG (SEQ ID NO: 20); and/or (c) a HC CDR3 comprising the amino acid sequence RLFSSTNI (SEQ ID NO: 21); and/or the LC comprises (a) a LC CDR1 comprising the amino acid sequence QASQSIYNNNWLS (SEQ ID NO: 22); and/or (b) a LC CDR2 comprising the amino acid sequence LASTLAS (SEQ ID NO: 12); and/or (c) a LC CDR3 comprising the amino acid sequence LGGESSSDDGIA (SEQ ID NO: 23).

In some aspects of the antibody, the HC comprises (a) a HC CDR1 comprising the amino acid sequence SHAIS (SEQ ID NO: 24); and/or (b) a HC CDR2 comprising the amino acid sequence TINSDSHTYYATWAKG (SEQ ID NO: 25); and/or (c) a HC CDR3 comprising the amino acid sequence RIFSSSNI (SEQ ID NO: 16); and/or the LC comprises (a) a LC CDR1 comprising the amino acid sequence QASQSIYNNNWLS (SEQ ID NO: 17); and/or (b) a LC CDR2 comprising the amino acid sequence LASTLAS (SEQ ID NO: 12); and/or (c) a LC CDR3 comprising the amino acid sequence IGGESSNTDGIA (SEQ ID NO: 26).

In some aspects of the antibody, the HC immunoglobulin variable domain sequence comprises the amino acid sequence of SEQ ID NO: 2, SEQ ID NO: 4, or SEQ ID NO: 6.

In some aspects of the antibody, the LC immunoglobulin variable domain sequence comprises the amino acid sequence of SEQ ID NO: 3, SEQ ID NO: 5, or SEQ ID NO: 7.

In some aspects of the antibody, the HC immunoglobulin variable domain sequence comprises the amino acid sequence of SEQ ID NO: 2, SEQ ID NO: 4, or SEQ ID NO: 6, and the LC immunoglobulin variable domain sequence comprises the amino acid sequence of SEQ ID NO: 3, SEQ ID NO: 5, or SEQ ID NO: 7.

In some aspects, the antibody further comprises a detectable label.

In some aspects, the antibody is a monoclonal antibody, a chimeric antibody or a humanized antibody.

In another aspect, provided herein is an antigen binding fragment of the antibodies disclosed herein, wherein the antigen binding fragment is selected from the group of Fab, F(ab')2, Fab', scF$_v$, or F$_v$.

In another aspect, provided herein is a composition comprising an antibody or antigen binding fragment as disclosed herein bound to a peptide comprising SEQ ID NO: 1, for example, a human PD-L1 protein or a fragment thereof. In an aspect, the peptide comprising SEQ ID NO: 1 is associated with a cell. For example, the composition may comprise a disaggregated cell sample labeled with an antibody or antibody fragment as disclosed herein, which composition is useful in, for example, affinity chromatography methods for isolating cells or for flow cytometry-based cellular analysis or cell sorting. As another example, the composition may comprise a fixed tissue sample or cell smear labeled with an antibody or antibody fragment as disclosed herein, which composition is useful in, for example, immunohistochemistry or cytology analysis. In another aspect, the antibody or the antibody fragment is bound to a solid support, which if useful in, for example: ELISAs; affinity chromatography or immunoprecipitation methods for isolating PD-L1 proteins or fragments thereof, PD-L1-positive cells, or complexes containing PD-L1 and other cellular components. In another aspect, the peptide comprising SEQ ID NO: 1 is bound to a solid support. For example, the peptide may be bound to the solid support via a secondary antibody specific for the peptide, which is useful in, for example, sandwich ELISAs. As another example, the peptide may be bound to a chromatography column, which is useful in, for example, isolation or purification of antibodies according to the present invention. In another aspect, the peptide is disposed in a solution, such as a lysis solution or a solution containing a sub-cellular fraction of a fractionated cell, which is useful in, for example, ELISAs and affinity chromatography or immunoprecipitation methods of isolating PD-L1 proteins or fragments thereof or complexes containing PD-L1 and other cellular components. In another aspect, the peptide is associated with a matrix, such as, for example, a gel electrophoresis gel or a matrix commonly used for western blotting (such as membranes made of nitrocellulose or polyvinylidene difluoride), which compositions are useful for electrophoretic and/or immunoblotting techniques, such as Western blotting.

In another aspect, provided herein is a method of detecting PD-L1 in a biological sample comprising, or alternatively consisting essentially of or yet further consisting of, contacting the sample with an antibody or antigen binding fragment as disclosed herein, and detecting a complex formed by the binding of the antibody or antigen binding fragment to PD-L1. In one aspect, the method further comprises, or alternatively consists essentially of, or yet further consisting of isolating the sample prior to contacting the sample with the antibody or antigen binding fragment.

In some aspects of the method, the sample comprises a cell or a tissue sample.

In some aspects of the method, the sample is obtained from a subject that is diagnosed as having, suspected as having, or at risk of having cancer.

In some aspects of the method, the cancer is selected from the group consisting of bladder transitional cell carcinoma, lung adenocarcinoma, breast ductal carcinoma, Hodgkin's lymphoma, pancreas adenocarcinoma, prostate adenocarcinoma, cervical squamous cell carcinoma, skin squamous cell carcinoma, and non-small cell lung cancer.

In some aspects of the method, the detection comprises one or more of immunohistochemistry (IHC), Western blotting, Flow cytometry or ELISA.

In another aspect, provided herein is a method of detecting a pathological cell in a sample isolated from a subject, comprising, or alternatively consisting essentially of, or yet further consisting of: (a) detecting the level of PD-L1 in a biological sample from the subject by detecting a complex formed by an antibody or antigen binding fragment of the present disclosure binding to PD-L1 in the sample; and (b) comparing the levels of PD-L1 observed in step (a) with the levels of PD-L1 observed in a control biological sample; wherein the pathological cell is detected when the level of PD-L1 is elevated compared to that observed in the control biological sample and the pathological cell is not detected when the level of PD-L1 is not elevated as compared to the observed in the control biological sample.

In some aspects of the method, the biological sample of the subject comprises one or more of a sample isolated from lung, kidney, bladder, breast, pancreas, prostate, cervix or skin.

In some aspects of the method, the detection comprises one or more of immunohistochemistry (IHC), Western Blotting, Flow cytometry or ELISA.

Additionally or alternatively, in some aspects, the methods disclosed herein further comprise isolating the biological sample from the subject prior to performance of the methods.

Additionally or alternatively, in some aspects of the methods, the subject is a mammal. In some aspects, the mammal is selected from the group of: a murine, feline, canine, ovine, bovine, simian, and a human.

In another aspect, provided herein is a PD-L1-specific antibody or antigen binding fragment thereof, wherein the antibody or antigen binding fragment has the same epitope specificity as an antibody as disclosed herein.

In a final aspect, provided herein is a kit for detecting PD-L1 comprising an antibody or antigen binding fragment as disclosed herein that optionally comprises instructions for use.

In one aspect, provided herein is a method of detecting PD-L1 in a tumor sample comprising (a) contacting the sample with an antibody or an antigen binding fragment of the antibody, wherein the antibody comprises a heavy chain (HC) immunoglobulin variable domain sequence and a light chain (LC) immunoglobulin variable domain sequence, wherein the antibody binds to an epitope of human PD-L1 comprising the amino acid sequence CGIQDTNSKKQS-DTHLEET (SEQ ID NO: 1) and/or has a half maximal effective concentration ($EC_{50}$) of at least $1.5 \times 10^{-11}$ M, wherein the HC comprises (i) a HC CDR1 comprising the amino acid sequence NHAIS (SEQ ID NO: 14); (ii) a HC CDR2 comprising the amino acid sequence TINSDTH-TYYATWPKG (SEQ ID NO: 15); and (iii) a HC CDR3 comprising the amino acid sequence RIFSSSNI (SEQ ID NO: 16); and the LC comprises (i) a LC CDR1 comprising the amino acid sequence QASQSIYNNNWLS (SEQ ID NO: 17); (ii) a LC CDR2 comprising the amino acid sequence LASTLAS (SEQ ID NO: 12); and (iii) a LC CDR3 comprising the amino acid sequence IGGESSNNDGIA (SEQ ID NO: 18); and (b) detecting a complex formed by the binding of the antibody or antigen binding fragment to PD-L1.

Further provided is an isolated polypeptide comprising, or alternatively consisting essentially of, or yet further consisting of, the amino acid sequence CGIQUINSKKQSDTI-ILEET (SEQ ID NO: 1), that are useful to generate antibodies that bind to PD-L1. In one aspect, the isolated polypeptides further comprise a label and/or contiguous polypeptide sequences (e.g., keyhole limpet haemocyanin (KLH) carrier protein) operatively coupled to the amino or carboxyl terminus.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 6B is an image showing the results of IHC on a FFPE stomach epithelium tissue section using anti-PD-L1 antibody E1L3N at a concentration of 0.44 µg/ml. FIG. 6C is an image showing the results of IHC on a FFPE stomach epithelium tissue section using anti-PD-L1 antibody E1L3N at a concentration of 1.75 µg/ml. FIG. 6D is an image showing the results of IHC on a FFPE stomach epithelium tissue section using anti-PD-L1 antibody E1L3N at a concentration of 7.0 µg/ml. FIG. 6E is an image showing the results of IHC on a FFPE stomach epithelium tissue section using anti-PD-L1 antibody E1L3N at a concentration of 28.0 µg/ml. FIG. 6F is an image showing the results of IHC on a FFPE nerve tissue section using anti-PD-L1 antibody E1L3N at a concentration of 0.11 µg/ml. FIG. 6G is an image showing the results of IHC on a FFPE nerve tissue section using anti-PD-L1 antibody E1L3N at a concentration of 0.44 µg/ml. FIG. 6H is an image showing the results of IHC on a FFPE nerve tissue section using anti-PD-L1 antibody E1L3N at a concentration of 1.75 µg/ml. FIG. 6I is an image showing the results of IHC on a FFPE nerve tissue section using anti-PD-L1 antibody E1L3N at a concentration of 7.0 µg/ml. FIG. 6J is an image showing the results of IHC on a FFPE nerve tissue section using anti-PD-L1 antibody E1L3N at a concentration of 28.0 µg/ml. FIG. 6K is an image showing the results of IHC on a FFPE stomach epithelium tissue section using anti-PD-L1 antibody SP263 at a concentration of 0.11 µg/ml. FIG. 6L is an image showing the results of IHC on a FFPE stomach epithelium tissue section using anti-PD-L1 antibody SP263 at a concentration of 0.44 µg/ml. FIG. 6M is an image showing the results of IHC on a FFPE stomach epithelium tissue section using anti-PD-L1 antibody SP263 at a concentration of 1.75 µg/ml. FIG. 6N is an image showing the results of IHC on a FFPE stomach epithelium tissue section using anti-PD-L1 antibody SP263 at a concentration of 7.0 µg/ml. FIG. 6O is an image showing the results of IHC on a FFPE stomach epithelium tissue section using anti-PD-L1 antibody SP263 at a concentration of 28.0 µg/ml. FIG. 6P is an image showing the results of IHC on a FFPE nerve tissue section using anti-PD-L1 antibody SP263 at a concentration of 0.11 µg/ml. FIG. 6Q is an image showing the results of IHC on a FFPE nerve tissue section using anti-PD-L1 antibody SP263 at a concentration of 0.44 µg/ml. FIG. 6R is an image showing the results of IHC on a FFPE nerve tissue section using anti-PD-L1 antibody SP263 at a concentration of 1.75 µg/ml. FIG. 6S is an image showing the results of IHC on a FFPE nerve tissue section using anti-PD-L1 antibody SP263 at a concentration of 7.0 µg/ml.

DETAILED DESCRIPTION

Figure 1:
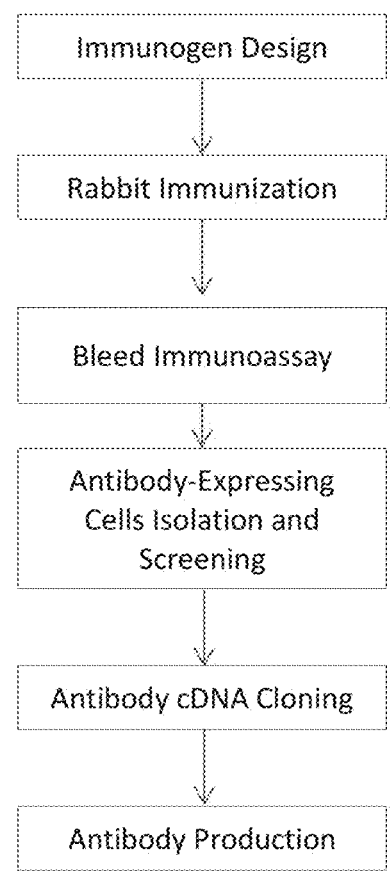
FIG. 1 shows a procedure for generating the monoclonal PD-L1 antibodies of the present disclosure.
Figure 2A:
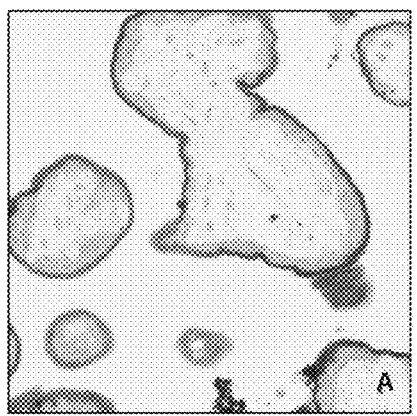
FIG. 2A is an image showing the results of immunohistochemistry (IHC) on a formalin-fixed, paraffin embedded (FFPE) placental tissue section using anti-PD-L1 antibody SP263.
Figure 2B:
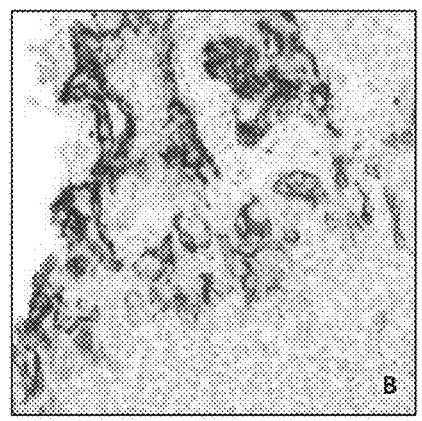
FIG. 2B is an image showing the results of IHC on a FFPE tonsil tissue section using anti-PD-L1 antibody SP263.
Figure 2C:
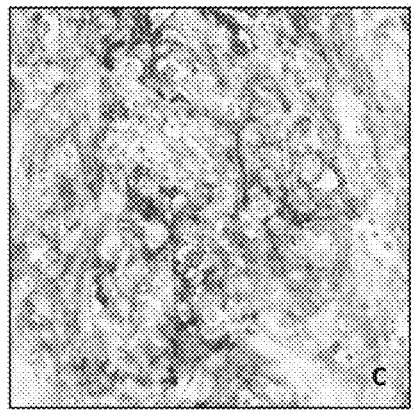
FIG. 2C is an image showing the results of IHC on a FFPE Hodgkin lymphoma tissue section using anti-PD-L1 antibody SP263.
Figure 2D:
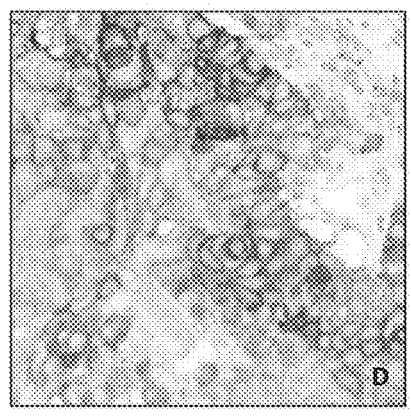
FIG. 2D is an image showing the results of IHC on a FFPE lung squamous cell carcinoma tissue section using anti-PD-L1 antibody SP263.

It is to be understood that this disclosure is not limited to particular aspects described, as such may, of course, vary. It is also to be understood that the terminology used herein is for the purpose of describing particular aspects only, and is not intended to be limiting, since the scope of the present disclosure will be limited only by the appended claims.

Unless defined otherwise, all technical and scientific terms used herein have the same meanings as commonly understood by one of ordinary skill in the art to which this disclosure belongs. Although any methods and materials similar or equivalent to those described herein can be used in the practice or testing of the present disclosure, the preferred methods, devices and materials are now described. All technical and patent publications cited herein are incorporated herein by reference in their entirety. Nothing herein is to be construed as an admission that the disclosure is not entitled to antedate such disclosure by virtue of prior disclosure.

The practice of the present technology will employ, unless otherwise indicated, conventional techniques of tissue culture, immunology, molecular biology, microbiology, cell biology and recombinant DNA, which are within the skill of the art. See, e.g., Sambrook and Russell eds. (2001) *Molecular Cloning: A Laboratory Manual*, 3rd edition; the series Ausubel et al. eds. (2007) *Current Protocols in Molecular Biology*; the series *Methods in Enzymology* (Academic Press, Inc., N.Y.); MacPherson et al. (1991) *PCR 1: A Practical Approach* (IRL Press at Oxford University Press); MacPherson et al. (1995) *PCR 2: A Practical Approach*; Harlow and Lane eds. (1999) *Antibodies, A Laboratory Manual*; Freshney (2005) *Culture of Animal Cells: A Manual of Basic Technique*, 5th edition; Gait ed. (1984) *Oligonucleotide Synthesis*; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology*.

All numerical designations, e.g., pH, temperature, time, concentration and molecular weight, including ranges, are approximations which are varied (+) or (−) by increments of 1.0 or 0.1, as appropriate, or alternatively by a variation of +/−15%, or alternatively 10%, or alternatively 5% or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

It is to be inferred without explicit recitation and unless otherwise intended, that when the disclosure relates to a polypeptide, protein, polynucleotide or antibody, an equivalent or a biologically equivalent of such is intended within the scope of this disclosure.

As used in the specification and claims, the singular form "a", "an" and "the" include plural references unless the context clearly dictates otherwise. For example, the term "a cell" includes a plurality of cells, including mixtures thereof.

As used herein, the "administration" of an agent or drug to a subject or subject includes any route of introducing or delivering to a subject a compound to perform its intended function. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated and target cell or tissue. Non-limiting examples of route of administration include oral administration, vaginal, nasal administration, injection, topical application and by suppository. Administration includes self-administration and the administration by another. It is also to be appreciated that the various modes of treatment or prevention of medical conditions as described are intended to mean "substantial", which includes total but also less than total treatment or prevention, and wherein some biologically or medically relevant result is achieved.

Administration can be effected in one dose, continuously or intermittently throughout the course of treatment. Methods of determining the most effective means and dosage of administration are known to those of skill in the art and will vary with the composition used for therapy, the purpose of the therapy, the target cell being treated and the subject being treated. Single or multiple administrations can be carried out with the dose level and pattern being selected by the treating physician.

As used herein, the term "animal" refers to living multicellular vertebrate organisms, a category that includes, for example, mammals and birds. The term "mammal" includes both human and non-human mammals. Similarly, the term "subject" or "patient" includes both human and veterinary subjects, for example, humans, non-human primates, dogs, cats, sheep, mice, horses, and cows.

As used herein, the term "antibody" collectively refers to immunoglobulins or immunoglobulin-like molecules including by way of example and without limitation, IgA, IgD, IgE, IgG and IgM, combinations thereof, and similar molecules produced during an immune response in any vertebrate, for example, in mammals such as humans, goats, rabbits and mice, as well as non-mammalian species, such as shark immunoglobulins. The term "antibody" includes intact immunoglobulins and "antibody fragments" or "antigen binding fragments" that specifically bind to a molecule of interest (or a group of highly similar molecules of interest) to the substantial exclusion of binding to other molecules (for example, antibodies and antibody fragments that have a binding constant for the molecule of interest that is at least $10^3$ $M^{-1}$ greater, at least $10^4$ $M^{-1}$ greater or at least $10^5$ $M^{-1}$ greater than a binding constant for other molecules in a biological sample). The term "antibody" also includes genetically engineered forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, J., *Immunology* $3^{rd}$ unology, Ed., W.H. Freeman & Co., New York, 1997.

More particularly, "antibody" refers to a polypeptide ligand comprising at least a light chain or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Typically, an immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, largely adopt β-sheet conformation and the CDRs form loops which connect, and in some cases form part of, the β-sheet structure. Thus, framework regions act to form a scaffold that provides for positioning the CDRs in correct orientation by inter-chain, non-covalent interactions.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds PD-L1 will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

The term "antibody" is further intended to encompass digestion fragments, specified portions, derivatives and variants thereof, including antibody mimetics or comprising portions of antibodies that mimic the structure and/or function of an antibody or specified fragment or portion thereof, including single chain antibodies and fragments thereof. Examples of binding fragments encompassed within the term "antigen binding portion" of an antibody include a Fab fragment, a monovalent fragment consisting of the $V_L$, $V_H$, $C_L$ and $C_H$, domains; a F(ab')$_2$ fragment, a bivalent fragment comprising two Fab fragments linked by a disulfide bridge at the hinge region; a $F_d$ fragment consisting of the $V_H$ and $C_H$, domains; a $F_v$ fragment consisting of the $V_L$ and $V_H$ domains of a single arm of an antibody, a dAb fragment (Ward et al. (1989) Nature 341:544-546), which consists of a $V_H$ domain; and an isolated complementarity determining region (CDR). Furthermore, although the two domains of the $F_v$ fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain $F_v$ (scF$_v$)). Bird et al. (1988) Science 242:423-426 and Huston et al. (1988) *Proc. Natl. Acad Sci. USA* 85:5879-5883. Single chain antibodies are also intended to be encompassed within the term "fragment of an antibody." Any of the above-noted antibody fragments are obtained using conventional techniques known to those of skill in the art, and the fragments are screened for binding specificity and neutralization activity in the same manner as are intact antibodies.

"Antibody fragments" or "antigen binding fragments" include proteolytic antibody fragments (such as F(ab')$_2$ fragments, Fab' fragments, Fab'-SH fragments and Fab fragments as are known in the art), recombinant antibody fragments (such as sF$_v$ fragments, dsF$_v$ fragments, bispecific sF$_v$ fragments, bispecific dsF$_v$ fragments, F(ab)'$_2$ fragments, single chain Fv proteins ("scF$_v$"), disulfide stabilized F$_v$ proteins ("dsF$_v$"), diabodies, and triabodies (as are known in the art), and camelid antibodies (see, for example, U.S. Pat. Nos. 6,015,695; 6,005,079; 5,874,541; 5,840,526; 5,800,988; and 5,759,808). An scF$_v$ protein is a fusion protein in which a light chain variable region of an immunoglobulin and a heavy chain variable region of an immunoglobulin are bound by a linker, while in dsF$_v$s, the chains have been mutated to introduce a disulfide bond to stabilize the association of the chains.

As used herein, the term "antibody derivative" is intended to encompass molecules that bind an epitope as defined herein and which are modifications or derivatives of an isolated PD-L1 antibody of this disclosure. Derivatives include, but are not limited to, for example, bispecific, heterospecific, trispecific, tetraspecific, multispecific antibodies, diabodies, chimeric, recombinant and humanized. As used herein, the term "bispecific molecule" is intended to include any agent, e.g., a protein, peptide, or protein or peptide complex, which has two different binding specificities. As used herein, the term "multispecific molecule" or "heterospecific molecule" is intended to include any agent, e.g., a protein, peptide, or protein or peptide complex, which has more than two different binding specificities. As used herein, the term "heteroantibodies" refers to two or more antibodies, antibody binding fragments (e.g., Fab), derivatives thereof, or antigen binding regions linked together, at least two of which have different specificities.

The term "antibody variant" is intended to include antibodies produced in a species other than a rabbit. It also includes antibodies containing post-translational modifications to the linear polypeptide sequence of the antibody or fragment. It further encompasses fully human antibodies.

As used herein, the term "antigen" refers to a compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, and proteins. Common categories of antigens include, but are not limited to, viral antigens, bacterial antigens, fungal antigens, protozoa and other parasitic antigens, tumor antigens, antigens involved in autoimmune disease, allergy and graft rejection, toxins, and other miscellaneous antigens.

As used herein, "binding affinity" refers to the tendency of one molecule to bind (typically non-covalently) with another molecule, such as the tendency of a member of a specific binding pair for another member of a specific binding pair. A binding affinity can be measured as a binding constant, which binding affinity for a specific binding pair (such as an antibody/antigen pair) can be at least $1 \times 10^{-5}$ M, at least $1 \times 10^{-6}$ M, at least $1 \times 10^{-7}$ M, at least $1 \times 10^{-8}$ M, at least $1 \times 10^{-9}$ M, at least $1 \times 10^{-10}$ M, at least $1 \times 10^{-11}$ M or at least $1 \times 10^{-12}$ M. In one aspect, binding affinity is calculated by a modification of the Scatchard method described by Frankel et al., *Mol. Immunol.*, 16:101-106, 1979. In another aspect, binding affinity is measured by an antigen/antibody dissociation rate. In yet another aspect, a high binding affinity is measured by a competition radioimmunoassay. In several examples, a high binding affinity for an antibody/antigen pair is at least about $1 \times 10^{-8}$ M. In other aspects, a high binding affinity is at least about $1.5 \times 10^{-8}$ M, at least about $2.0 \times 10^{-8}$ M, at least about $2.5 \times 10^{-8}$ M, at least about $3.0 \times 10^{-8}$ M, at least about $3.5 \times 10^{-8}$ M, at least about $4.0 \times 10^{-8}$ M, at least about $4.5 \times 10^{-8}$ M, or at least about $5.0 \times 10^{-8}$ M.

As used herein, the term "biological equivalent thereof" is intended to be synonymous with "equivalent thereof" when referring to a reference protein, antibody, polypeptide, polynucleotide or nucleic acid, and intends those having minimal homology while still maintaining desired structure or functionality. Unless specifically recited herein, it is contemplated that any nucleic acid, polynucleotide, polypeptide, protein or antibody mentioned herein also includes equivalents thereof. For example, an equivalent intends at least about 80% homology or identity and alternatively, at least about 85%, or alternatively at least about 90%, or alternatively at least about 95%, or alternatively 98% percent homology or identity and exhibits substantially equivalent biological activity to the reference protein, polypeptide, antibody or nucleic acid.

In one aspect, the term "equivalent" or "biological equivalent" of an antibody means the ability of the antibody to selectively bind its epitope protein or fragment thereof as measured by ELISA, IHC or other suitable methods. Biologically equivalent antibodies include, but are not limited to, those antibodies, peptides, antibody fragments, antibody variant, antibody derivative and antibody mimetics that bind to the same epitope as the reference antibody. The skilled artisan can prepare an antibody functionally equivalent to the antibodies of the present disclosure by introducing appropriate mutations into the antibody using site-directed mutagenesis (Hashimoto-Gotoh, T. et al., *Gene* 152, 271-275 (1995); Zoller & Smith, *Methods Enzymol.* 100, 468-500 (1983); Kramer, W. et al., *Nucleic Acids Res.* 12, 9441-9456 (1984); Kramer W. & Fritz H J., *Methods. Enzymol.* 154, 350-367 (1987); Kunkel, T A., *Proc Natl Acad Sci USA.* 82, 488-492 (1985); and Kunkel *Methods Enzymol.* 85, 2763-2766 (1988)).

Antibodies that are functionally equivalent to the antibodies of the present disclosure and comprise an amino acid sequence comprising mutation of one or more amino acids in the amino acid sequence of an antibody of the present disclosure are also included in the antibodies of the present disclosure. In such mutants, the number of amino acids that are mutated is generally 50 amino acids or less, preferably 30 or less, and more preferably 10 or less (for example, 5 amino acids or less). An amino acid residue is preferably mutated into one that conserves the properties of the amino acid side chain. For example, based on their side chain properties, amino acids are classified into: hydrophobic amino acids (A, I, L, M, F, P, W, Y, and V); hydrophilic amino acids (R, D, N, C, E, Q, G, H, K, S, and T); amino acids having aliphatic side-chains (G, A, V, L, I, and P); amino acids having hydroxyl group-containing side-chains (S, T, and Y); amino acids having sulfur atom-containing side-chains (C and M); amino acids having carboxylic acid- and amide-containing side-chains (D, N, E, and Q); base-containing side-chains (R, K, and H); and amino acids having aromatic-containing side-chains (H, F, Y, and W).

(The letters within parentheses indicate one-letter amino acid codes)

As used herein, the term "biological sample" means sample material derived from or contacted by living cells. The term "biological sample" is intended to include tissues, cells and biological fluids isolated from a subject, as well as tissues, cells and fluids present within a subject. Biological samples of the disclosure include, e.g., but are not limited to, whole blood, plasma, semen, saliva, tears, urine, fecal material, sweat, buccal, skin, cerebrospinal fluid, and hair. Biological samples can also be obtained from biopsies of internal organs or from cancers. Biological samples can be obtained from subjects for diagnosis or research or can be obtained from healthy individuals, as controls or for basic research.

The terms "cancer," "neoplasm," and "tumor," used interchangeably and in either the singular or plural form, refer to cells that have undergone a malignant transformation that makes them pathological to the host organism and are selected from the group consisting of bladder transitional cell carcinoma, lung adenocarcinoma, breast ductal carcinoma, Hodgkin's lymphoma, pancreas adenocarcinoma, prostate adenocarcinoma, cervical squamous cell carcinoma, skin squamous cell carcinoma, and non-small cell lung cancer.

Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by such procedures as CAT scan, magnetic resonance imaging (MRI), X-ray, ultrasound or palpation. Biochemical or immunologic findings alone may be insufficient to meet this definition.

A neoplasm is an abnormal mass or colony of cells produced by a relatively autonomous new growth of tissue. Most neoplasms arise from the clonal expansion of a single cell that has undergone neoplastic transformation. The transformation of a normal to a neoplastic cell can be caused by a chemical, physical, or biological agent (or event) that directly and irreversibly alters the cell genome. Neoplastic cells are characterized by the loss of some specialized functions and the acquisition of new biological properties, foremost, the property of relatively autonomous (uncontrolled) growth. Neoplastic cells pass on their heritable biological characteristics to progeny cells.

The past, present, and future predicted biological behavior, or clinical course, of a neoplasm is further classified as benign or malignant, a distinction of great importance in diagnosis, treatment, and prognosis. A malignant neoplasm manifests a greater degree of autonomy, is capable of invasion and metastatic spread, may be resistant to treatment, and may cause death. A benign neoplasm has a lesser degree of autonomy, is usually not invasive, does not metastasize, and generally produces no great harm if treated adequately.

Cancer is a generic term for malignant neoplasms. Anaplasia is a characteristic property of cancer cells and denotes a lack of normal structural and functional characteristics (undifferentiation).

A tumor is literally a swelling of any type, such as an inflammatory or other swelling, but modem usage generally denotes a neoplasm.

Histogenesis is the origin of a tissue and is a method of classifying neoplasms on the basis of the tissue cell of origin. Adenomas are benign neoplasms of glandular epithelium. Carcinomas are malignant tumors of epithelium. Sarcomas are malignant tumors of mesenchymal tissues. One system to classify neoplasia utilizes biological (clinical) behavior, whether benign or malignant, and the histogenesis, the tissue or cell of origin of the neoplasm as determined by histologic and cytologic examination. Neoplasms may originate in almost any tissue containing cells capable of mitotic division. The histogenetic classification of neoplasms is based upon the tissue (or cell) of origin as determined by histologic and cytologic examination.

As used herein, the term "chimeric antibody" means an antibody in which the Fc constant region of a monoclonal antibody from one species (e.g., a mouse Fc constant region) is replaced, using recombinant DNA techniques, with an Fe constant region from an antibody of another species (e.g., a human Fc constant region). See generally, Robinson et al., PCT/US86/02269; Akira et al., European Patent Application 184,187; Taniguchi, European Patent Application 171,496; Morrison et al., European Patent Application 173,494; Neuberger et al., WO 86/01533; Cabilly et al. U.S. Pat. No. 4,816,567; Cabilly et al., European Patent Application 125, 023; Better et al., *Science* 240: 1041-1043, 1988; Liu et al., *Proc. Natl. Acad. Sci. USA* 84: 3439-3443, 1987; Liu et al., *J. Immunol.* 139: 3521-3526, 1987; Sun et al., *Proc. Natl. Acad. Sci. USA* 84: 214-218, 1987; Nishimura et al., *Cancer Res* 47: 999-1005, 1987; Wood et al., *Nature* 314: 446-449, 1885; and Shaw et al., *J. Natl. Cancer Inst.* 80: 1553-1559, 1988. In certain aspects the target binding region or site will be from a non-human source (e.g. mouse or primate) and the constant region is human.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. For example, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this disclosure. Aspects defined by each of these transition terms are within the scope of this disclosure.

A "control" biological sample is an alternative sample used in an experiment for comparison purpose. A control can be "positive" or "negative". For example, where the purpose of the experiment is to determine a correlation of the efficacy of a therapeutic agent for the treatment for a particular type of cancer, it is generally preferable to use a positive control (a compound or composition known to exhibit the desired therapeutic effect) and a negative control (a subject or a sample that does not receive the therapy or receives a placebo).

As used herein, the term "detectable label" refers to a molecule or material that can produce a detectable (such as visually, electronically or otherwise) signal that indicates the presence and/or concentration of the label in a sample. When conjugated to a specific binding molecule, the detectable label can be used to locate and/or quantify the target to which the specific binding molecule is directed. Thereby, the presence and/or concentration of the target in a sample can be detected by detecting the signal produced by the detectable label. A detectable label can be detected directly or indirectly, and several different detectable labels conjugated to different specific-binding molecules can be used in combination to detect one or more targets. For example, a first detectable label conjugated to an antibody specific to a target can be detected indirectly through the use of a second detectable label that is conjugated to a molecule that specifically binds the first detectable label. Multiple detectable labels that can be separately detected can be conjugated to different specific binding molecules that specifically bind different targets to provide a multiplexed assay that can provide simultaneous detection of the multiple targets in a sample. A detectable signal can be generated by any mechanism including absorption, emission and/or scattering of a photon (including radio frequency, microwave frequency, infrared frequency, visible frequency and ultra-violet frequency photons). Detectable labels include colored, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected through antibody-hapten binding interactions using additional detectably labeled antibody conjugates, and paramagnetic and magnetic molecules or materials. Particular examples of detectable labels include enzymes such as horseradish peroxidase, alkaline phosphatase, acid phosphatase, glucose oxidase, β-galactosidase or β-glucuronidase; fluorphores such as fluoresceins, luminophores, coumarins, BODIPY dyes, resorufins, and rhodamines (many additional examples of fluorescent molecules can be found in *The Handbook—A Guide to Fluorescent Probes and Labeling Technologies*, Molecular Probes, Eugene, Oreg.); nanoparticles such as quantum dots (obtained, for example, from QuantumDot Corp, Invitrogen Nanocrystal Technologies, Hayward, Calif.; see also, U.S. Pat. Nos. 6,815,064, 6,682,596 and 6,649,138, each of which patents is incorporated by reference herein); metal chelates such as DOTA and DPTA chelates of radioactive or paramagnetic metal ions like $Gd^{3+}$; and liposomes, for example, liposomes containing trapped fluorescent molecules. Where the detectable label includes an enzyme, a detectable substrate such as a chromogen, a fluorogenic compound, or a luminogenic compound can be used in combination with the enzyme to generate a detectable signal (A wide variety of such compounds are commercially available, for example, from Invitrogen Corporation, Eugene Oreg.). Particular examples of chromogenic compounds include diaminobenzidine (DAB), 4-nitrophenylphospate (pNPP), fast red, bromochloroindolyl phosphate (BCIP), nitro blue tetrazolium (NBT), BCIP/NBT, fast red, AP Orange, AP blue, tetramethylbenzidine (TMB), 2,2'-azino-di-[3-ethylbenzothiazoline sulphonate] (ABTS), o-dianisidine, 4-chloronaphthol (4-CN), nitrophenyl-β-D-galactopyranoside (ONPG), o-phenylenediamine (OPD), 5-bromo-4-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), 3-amino-9-ethyl carbazol (AEC), fuchsin, iodonitrotetrazolium (INT), tetrazolium blue and tetrazolium violet. Alternatively, an enzyme can be used in a metallographic detection scheme. Metallographic detection methods include using an enzyme such as alkaline phosphatase in combination with a water-soluble metal ion and a redox-inactive substrate of the enzyme. The substrate is converted to a redox-active agent by the enzyme, and the redox-active agent reduces the metal ion, causing it to form a detectable precipitate. (See, for example, co-pending U.S. patent application Ser. No. 11/015,646, filed Dec. 20, 2004, PCT Publication No. 2005/003777 and U.S. Patent Application Publication No. 2004/0265922; each of which is incorporated by reference herein). Metallographic detection methods include using an oxido-reductase enzyme (such as horseradish peroxidase) along with a water soluble metal ion, an oxidizing agent and a reducing agent, again to form a detectable precipitate. (See, for example, U.S. Pat. No. 6,670,113, which is incorporated by reference herein). Haptens are small molecules that are specifically bound by antibodies, although by themselves they will not elicit an immune response in an animal and must first be attached to a larger carrier molecule such as a protein to generate an immune response. Examples of haptens include di-nitrophenyl, biotin, digoxigenin, and fluorescein. Additional examples of oxazole, pyrazole, thiazole, nitroaryl, benzofuran, triperpene, urea, thiourea, rotenoid, coumarin and cyclolignan haptens are disclosed in U.S. Provisional Patent Application No. 60/856,133, filed Nov. 1, 2006, which is incorporated by reference herein. In an illustrative example, the detectable label comprises a non-endogenous hapten (e.g. not biotin), such as, for example, the haptens disclosed in U.S. Pat. Nos. 7,695,929, 8,618,265 and 8,846,320 (incorporated herein by reference), including for example pyrazoles, nitrophenyl compounds, benzofurazans, triterpenes, ureas and thioureas, rotenone and rotenone derivatives, oxazoles and thiazoles, coumarin and coumarin derivatives, and cyclolignans. Such detectable labels can be detected using antibodies or antigen-binding fragments thereof capable of binding to the hapten.

As used herein, an "epitope" or "antigenic determinant" refers to particular chemical groups or contiguous or non-contiguous peptide sequences on a molecule that are antigenic, i.e., that elicit a specific immune response. An antibody binds a particular antigenic epitope. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell. The expression level of a gene may be determined by measuring the amount of mRNA or protein in a cell or tissue sample. In one aspect, the expression level of a gene from one sample may be directly compared to the expression level of that gene from a control or reference sample. In another aspect, the expression level of a gene from one sample may be directly compared to the expression level of that gene from the same sample following administration of a compound.

As used herein, "homology" or "identical", percent "identity" or "similarity", when used in the context of two or more nucleic acids or polypeptide sequences, refers to two or more sequences or subsequences that are the same or have a specified percentage of nucleotides or amino acid residues that are the same, e.g., at least 60% identity, preferably at least 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein). Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST. The terms "homology" or "identical", percent "identity" or "similarity" also refer to, or can be applied to, the complement of a test sequence. The terms also include sequences that have deletions and/or additions, as well as those that have substitutions. As described herein, the preferred algorithms can account for gaps and the like. Preferably, identity exists over a region that is at least about 25 amino acids or nucleotides in length, or more preferably over a region that is at least 50-100 amino acids or nucleotides in length. An "unrelated" or "non-homologous" sequence shares less than 40% identity, or alternatively less than 25% identity, with one of the sequences of the present disclosure.

The term "human antibody" as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a rabbit, have been grafted onto human framework sequences. Thus, as used herein, the term "human antibody" refers to an antibody in which substantially every part of the protein (e.g., CDR, framework, $C_L$, $C_H$ domains (e.g., $C_{H1}$, $C_{H2}$, $C_{H3}$), hinge, $V_L$, $V_H$) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an $F_v$ can comprise a linker peptide, such as two to about eight glycine or other amino acid residues, which connects the variable region of the heavy chain and the variable region of the light chain. Such linker peptides are considered to be of human origin.

As used herein, the term "humanized antibody" refers to an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

As used herein, the term "humanized immunoglobulin" refers to an immunoglobulin including a human framework region and one or more CDRs from a non-human (for example a mouse, rat, rabbit or synthetic) immunoglobulin. The non-human immunoglobulin providing the CDRs is termed a "donor," and the human immunoglobulin providing the framework is termed an "acceptor." In one aspect, all the CDRs are from the donor immunoglobulin in a humanized immunoglobulin. Constant regions need not be present, but if they are, they must be substantially identical to human immunoglobulin constant regions, i.e., at least about 85-90%, or at least about 95% or more identical. Hence, all parts of a humanized immunoglobulin, except possibly the CDRs, are substantially identical to corresponding parts of natural human immunoglobulin sequences.

The term "isolated" as used herein refers to molecules or biological or cellular materials being substantially free from other materials. In one aspect, the term "isolated" refers to nucleic acid, such as DNA or RNA, or protein or polypeptide (e.g., an antibody or derivative thereof), or cell or cellular organelle, or tissue or organ, separated from other DNAs or RNAs, or proteins or polypeptides, or cells or cellular organelles, or tissues or organs, respectively, that are present in the natural source. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides. The term "isolated" is also used herein to refer to cells or tissues that are isolated from other cells or tissues and is meant to encompass both cultured and engineered cells or tissues.

As used herein, the term "monoclonal antibody" refers to an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

As used herein, a "pathological cell" is one that is pertaining to or arising from disease. Pathological cells can be hyperproliferative. A "hyperproliferative cell" means cells or tissue are dividing and growing at a rate greater than that when the cell or tissue is in a normal or healthy state. Examples of such include, but are not limited to precancerous (i.e., epithelial dysplasia) and cancer cells. Hyperproliferative cells also include de-differentiated, immortalized, neoplastic, malignant, metastatic, and cancer cells such as sarcoma cells, leukemia cells, carcinoma cells, or adenocarcinoma cells.

As used herein, "PD-L1" (Programmed death ligand-1) or "B7-H1" (Human B7 homolog 1), or PDCD1L1 (Programmed cell death 1 ligand 1) is a member of the growing B7 family of immune proteins that provide signals for both stimulating and inhibiting T cell activation. Human PD-L1 encodes a 290 amino acid (aa) type I membrane precursor protein with a putative 18 aa signal peptide, a 221 aa extracellular domain, a 21 aa transmembrane region, and a 31 aa cytoplasmic domain (Entrez Gene ID: 29126, UniProtKB: Q9NZQ7).

The term "protein", "peptide" and "polypeptide" are used interchangeably and in their broadest sense to refer to a compound of two or more subunit amino acids, amino acid analogs or peptidomimetics. The subunits may be linked by peptide bonds. In another aspect, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any aspect of this disclosure that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

As used herein, the term "purified" does not require absolute purity; rather, it is intended as a relative term. Thus, for example, a purified nucleic acid, peptide, protein, biological complexes or other active compound is one that is isolated in whole or in part from proteins or other contaminants. Generally, substantially purified peptides, proteins, biological complexes, or other active compounds for use within the disclosure comprise more than 80% of all macromolecular species present in a preparation prior to admixture or formulation of the peptide, protein, biological complex or other active compound with a pharmaceutical carrier, excipient, buffer, absorption enhancing agent, stabilizer, preservative, adjuvant or other co-ingredient in a complete pharmaceutical formulation for therapeutic administration. More typically, the peptide, protein, biological complex or other active compound is purified to represent greater than 90%, often greater than 95% of all macromolecular species present in a purified preparation prior to admixture with other formulation ingredients. In other cases, the purified preparation may be essentially homogeneous, wherein other macromolecular species are not detectable by conventional techniques.

As used herein, the term "specific binding" means the contact between an antibody and an antigen with a binding affinity of at least $10^{-6}$ M. In certain aspects, antibodies bind with affinities of at least about $10^{-7}$ M, and preferably $10^{-8}$ M, $10^{-9}$ M, $10^{-10}$ M, $10^{-11}$ M, or $10^{-12}$ M.

As used herein, the term "recombinant protein" refers to a polypeptide which is produced by recombinant DNA techniques, wherein generally, DNA encoding the polypeptide is inserted into a suitable expression vector which is in turn used to transform a host cell to produce the heterologous protein.

As used herein, "treating" or "treatment" of a disease in a subject refers to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of this disclosure, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable. Preferred are compounds that are potent and can be administered locally at very low doses, thus minimizing systemic adverse effects.

Modes for Carrying Out the Disclosure

Antibodies and Antibody Fragments

The general structure of antibodies is known in the art and will only be briefly summarized here. An immunoglobulin monomer comprises two heavy chains and two light chains connected by disulfide bonds. Each heavy chain is paired with one of the light chains to which it is directly bound via a disulfide bond. Each heavy chain comprises a constant region (which varies depending on the isotype of the antibody) and a variable region. The variable region comprises three hypervariable regions (or complementarity determining regions) which are designated CDRH1, CDRH2 and CDRH3 and which are supported within framework regions. Each light chain comprises a constant region and a variable region, with the variable region comprising three hypervariable regions (designated CDRL1, CDRL2 and CDRL3) supported by framework regions in an analogous manner to the variable region of the heavy chain.

The hypervariable regions of each pair of heavy and light chains mutually cooperate to provide an antigen binding site that is capable of binding a target antigen. The binding specificity of a pair of heavy and light chains is defined by the sequence of CDR1, CDR2 and CDR3 of the heavy and light chains. Thus once a set of CDR sequences (i.e. the sequence of CDR1, CDR2 and CDR3 for the heavy and light chains) is determined which gives rise to a particular binding specificity, the set of CDR sequences can, in principle, be inserted into the appropriate positions within any other antibody framework regions linked with any antibody constant regions in order to provide a different antibody with the same antigen binding specificity.

With the above in mind, in one aspect, provided herein is an isolated antibody comprising a heavy chain (HC) immunoglobulin variable domain sequence and a light chain (LC) immunoglobulin variable domain sequence, wherein the heavy chain and light chain immunoglobulin variable domain sequences form an antigen binding site that binds to an epitope of human PD-L1 comprising the amino acid sequence CGIQDTNSKKQSDTHLEET (SEQ ID NO: 1) and/or has a half maximal effective concentration ($EC_{50}$) of at least $1.5 \times 10^{-11}$ M.

In one aspect, the sequences of CDR3 of the heavy and light chains of the PD-L1 antibodies of the present disclosure conform with the consensus sequences set out in SEQ ID NOS: 10 and 13.

In one aspect, the sequences of CDR1 and CDR2 of the heavy chain of the PD-L1 antibodies of the present disclosure conform with the consensus sequences set out in SEQ ID NOS: 8 and 9.

In another aspect, the sequences of CDR1 of the light chain of the PD-L1 antibodies of the present disclosure conform with the consensus sequence set out in SEQ ID NO: 11.

In another aspect, the sequence of CDR2 of the light chain of the PD-L1 antibodies of the present disclosure comprises the sequence of SEQ ID NO: 12.

In another aspect, the PD-L1 antibodies of the present disclosure has the CDR3 sequence of the light chain conforming with the consensus sequence of SEQ ID NO: 13 and the CDR3 sequence of the heavy chain conforming with the consensus sequence of SEQ ID NO: 10.

Specific CDR1, CDR2 and CDR3 sequences from some of the preferred antibodies (SP263, J45H2L4 and J27H6L4) of the disclosure are set out in Table 1. Thus, the present disclosure provides antibodies comprising CDRs 1 to 3 having the sequences from these preferred antibodies. However, since there is a high level of sequence identity between sequences of the preferred antibodies of the disclosure, it is also within the scope of the disclosure to provide antibodies with CDR sequences from different preferred antibodies. For example, also included in the disclosure is an antibody comprising a heavy chain having the sequence of CDR1 from J27H6L4, CDR2 from J45H2L4 and CDR3 from SP263 and light chain having the sequence of CDR1 from J45H2L4, CDR2 from SP263 and CDR3 from J27H6L4.

In another aspect of the disclosure, the isolated antibody includes one or more of the following characteristics:

(a) the LC immunoglobulin variable domain sequence comprises one or more CDRs that are at least 85% identical to a CDR of a LC variable domain of SP263, J45H2L4 or J27H6L4;

(b) the HC immunoglobulin variable domain sequence comprises one or more CDRs that are at least 85% identical to a CDR of a HC variable domain of SP263, J45H2L4 or J27H6L4;

(c) the LC immunoglobulin variable domain sequence is at least 85% identical to a LC variable domain of SP263, J45H2L4 or J27H6L4;

(d) the HC immunoglobulin variable domain sequence is at least 85% identical to a HC variable domain of SP263, J45H2L4 or J27H6L4; and (e) the antibody binds an epitope that overlaps with an epitope bound by SP263, J45H2L4 or J27H6L4.

In one aspect, the disclosure provides an isolated antibody that is at least 85% identical to an antibody selected from the group consisting of SP263, J45H2L4 and J27H6L4. In one aspect, the disclosure provides an isolated antibody selected from the group consisting of SP263, J45H2L4 and J27H6L4.

In one aspect, the disclosure provides an isolated antibody comprising the CDRs of SP263. In one aspect the disclosure provides an isolated antibody that is at least 85% identical to SP263. The CDRs of SP263 are represented in Table 1.

In one aspect, the disclosure provides an isolated antibody comprising the CDRs of J45H2L4. In one aspect the disclosure provides an isolated antibody that is at least 85% identical to J45H2L4. The CDRs of J45H2L4 are represented in Table 1.

In one aspect, the disclosure provides an isolated antibody comprising the CDRs of J27H6L4. In one aspect the disclosure provides an isolated antibody that is at least 85% identical to J27H6L4. The CDRs of J27H6L4 are represented in Table 1.

In some aspects of the antibodies provided herein, the HC variable domain sequence comprises a variable domain sequence of SP263 and the LC variable domain sequence comprises a variable domain sequence of SP263.

In some aspects of the antibodies provided herein, the HC variable domain sequence comprises a variable domain sequence of J45H2L4 and the LC variable domain sequence comprises a variable domain sequence of J45H2L4.

In some aspects of the antibodies provided herein, the HC variable domain sequence comprises a variable domain sequence of J27H6L4 and the LC variable domain sequence comprises a variable domain sequence of J27H6L4.

In some of the aspects of the antibodies provided herein, the antibody binds human PD-L1 with a dissociation constant ($K_D$) of less than $10^{-4}$ M, $10^{-5}$ M, $10^{-6}$ M, $10^{-7}$ M, $10^{-8}$ M, $10^{-9}$ M, $10^{-10}$ M, $10^{-11}$ M, or $10^{-12}$ M. In some of the aspects of the antibodies provided herein, the antigen binding site specifically binds to human PD-L1.

In some of the aspects of the antibodies provided herein, the antibody is soluble Fab.

In some of the aspects of the antibodies provided herein, the HC and LC variable domain sequences are components of the same polypeptide chain. In some of the aspects of the antibodies provided herein, the HC and LC variable domain sequences are components of different polypeptide chains.

In some of the aspects of the antibodies provided herein, the antibody is a full-length antibody.

In some of the aspects of the antibodies provided herein, the antibody is a monoclonal antibody.

In some of the aspects of the antibodies provided herein, the antibody is chimeric or humanized.

In some of the aspects of the antibodies provided herein, the antibody is selected from the group consisting of Fab, F(ab)'2, Fab', scF$_v$, and F$_v$.

In some of the aspects of the antibodies provided herein, the antibody comprises an Fc domain. In some of the aspects of the antibodies provided herein, the antibody is a rabbit antibody. In some of the aspects of the antibodies provided herein, the antibody is a human or humanized antibody or is non-immunogenic in a human.

In some of the aspects of the antibodies provided herein, the antibody comprises a human antibody framework region.

In other aspects, one or more amino acid residues in a CDR of the antibodies provided herein are substituted with another amino acid. The substitution may be "conservative" in the sense of being a substitution within the same family of amino acids. The naturally occurring amino acids may be divided into the following four families and conservative substitutions will take place within those families.

1) Amino acids with basic side chains: lysine, arginine, histidine.
2) Amino acids with acidic side chains: aspartic acid, glutamic acid
3) Amino acids with uncharged polar side chains: asparagine, glutamine, serine, threonine, tyrosine.
4) Amino acids with nonpolar side chains: glycine, alanine, valine, leucine, isoleucine, proline, phenylalanine, methionine, tryptophan, cysteine.

In another aspect, one or more amino acid residues are added to or deleted from one or more CDRs of an antibody. Such additions or deletions occur at the N or C termini of the CDR or at a position within the CDR.

By varying the amino acid sequence of the CDRs of an antibody by addition, deletion or substitution of amino acids, various effects such as increased binding affinity for the target antigen may be obtained.

It is to be appreciated that antibodies of the disclosure comprising such varied CDR sequences still bind PD-L1 with similar specificity and sensitivity profiles as SP263, J45H2L4 and J27H6L4. This may be tested by way of the binding assays disclosed in Examples described herein.

The constant regions of antibodies may also be varied from those specifically disclosed for antibodies SP263, J45H2L4 and J27H6L4. For example, antibodies may be provided with Fc regions of any isotype: IgA (IgA1, IgA2), IgD, IgE, IgG (IgG1, IgG2, IgG3, IgG4) or IgM. Non-limiting examples of constant region sequences include:

```
Human IgD constant region, Uniprot: P01880
                                                        SEQ ID NO: 27
APTKAPDVFPIISGCRHPKDNSPVVLACLITGYHPTSVTVTWYMGTQSQPQRTFPEIQRR

DSYYMTSSQLSTPLQQWRQGEYKCVVQHTASKSKKEIFRWPESPKAQASSVPTAQPQA

EGSLAKATTAPATTRNTGRGGEEKKKEKEKEEQEERETKTPECPSHTQPLGVYLLTPAV

QDLWLRDKATFTCFVVGSDLKDAHLTWEVAGKVPTGGVEEGLLERHSNGSQSQHSRLT

LPRSLWNAGTSVTCTLNHPSLPPQRLMALREPAAQAPVKLSLNLLASSDPPEAASWLLC

EVSGFSPPNILLMWLEDQREVNTSGFAPARPPPQPGSTTFWAWSVLRVPAPPSPQPATYT

CVVSHEDSRTLLNASRSLEVSYVTDHGPMK

Human IgG1 constant region, Uniprot: P01857
                                                        SEQ ID NO: 28
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPSR
```

DELTKNQVSLTCLVKGFYPSDIAVEWESNGQPENNYKTTPPVLDSDGSFFLYSKLTVDK

SRWQQGNVFSCSVMHEALHNHYTQKSLSLSPGK

Human IgG2 constant region, Uniprot: P01859
SEQ ID NO: 29
ASTKGPSVFPLAPCSRSTSESTAALGCLVKDYFPEPVTVSWNSGALTSGVHTFPAVLQSS

GLYSLSSVVTVPSSNFGTQTYTCNVDHKPSNTKVDKTVERKCCVECPPCPAPPVAGPSV

FLFPPKPKDILMISRTPEVTCVVVDVSHEDPEVQFNWYVDGVEVHNAKTKPREEQFNST

FRVVSVLTVVHQDWLNGKEYKCKVSNKGLPAPIEKTISKTKGQPREPQVYTLPPSREEM

TKNQVSLTCLVKGFYPSDISVEWESNGQPENNYKTTPPMLDSDGSFFLYSKLTVDKSRW

QQGNVFSCSVMHEALHNHYTQKSLSLSPGK

Human IgG3 constant region, Uniprot: P01860
SEQ ID NO: 30
ASTKGPSVFPLAPCSRSTSGGTAALGCLVKDYFPEPVTVSWNSGALTSGVHTFPAVLQSS

GLYSLSSVVTVPSSSLGTQTYTCNVNHKPSNTKVDKRVELKTPLGDTTHTCPRCPEPKSC

DTPPPCPRCPEPKSCDTPPPCPRCPEPKSCDTPPPCPRCPAPELLGGPSVFLFPPKPKDTLMI

SRTPEVTCVVVDVSHEDPEVQFKWYVDGVEVHNAKTKPREEQYNSTFRVVSVLTVLHQ

DWLNGKEYKCKVSNKALPAPIEKTISKTKGQPREPQVYTLPPSREEMTKNQVSLTCLVK

GFYPSDIAVEWESSGQPENNYNTTPPMLDSDGSFFLYSKLTVDKSRWQQGNIFSCSVMH

EALHNRFTQKSLSLSPGK

Human IgM constant region, Uniprot: P01871
SEQ ID NO: 31
GSASAPTLFPLVSCENSPSDTSSVAVGCLAQDFLPDSITLSWKYKNNSDISSTRGFPSVLR

GGKYAATSQVLLPSKDVMQGTDEHVVCKVQHPNGNKEKNVPLPVIAELPPKVSVFVPP

RDGFFGNPRKSKLICQATGFSPRQIQVSWLREGKQVGSGVTTDQVQAEAKESGPTTYKV

TSTLTIKESDWLGQSMFTCRVDHRGLTFQQNASSMCVPDQDTAIRVFAIPPSFASIFLTKS

TKLTCLVTDLTTYDSVTISWTRQNGEAVKTHTNISESHPNATFSAVGEASICEDDWNSGE

RFTCTVTHTDLPSPLKQTISRPKGVALHRPDVYLLPPAREQLNLRESATITCLVTGFSPAD

VFVQWMQRGQPLSPEKYVTSAPMPEPQAPGRYFAHSILTVSEEEWNTGETYTCVAHEA

LPNRVTERTVDKSTGKPTLYNVSLVMSDTAGTCY

Human IgG4 constant region, Uniprot: P01861
SEQ ID NO: 32
ASTKGPSVFPLAPCSRSTSESTAALGCLVKDYFPEPVTVSWNSGALTSGVHTFPAVLQSS

GLYSLSSVVTVPSSSLGTKTYTCNVDHKPSNTKVDKRVESKYGPPCPSCPAPEFLGGPSV

FLFPPKPKDTLMISRTPEVTCVVVDVSQEDPEVQFNWYVDGVEVHNAKTKPREEQFNST

YRVVSVLTVLHQDWLNGKEYKCKVSNKGLPSSIEKTISKAKGQPREPQVYTLPPSQEEM

TKNQVSLTCLVKGFYPSDIAVEWESNGQPENNYKTTPPVLDSDGSFFLYSRLTVDKSRW

QEGNVFSCSVMHEALHNHYTQKSLSLSLGK

Human IgA1 constant region, Uniprot: P01876
SEQ ID NO: 33
ASPTSPKVFPLSLCSTQPDGNVVIACLVQGFFPQEPLSVTWSESGQGVTARNFPPSQDAS

GDLYTTSSQLTLPATQCLAGKSVTCHVKHYTNPSQDVTVPCPVPSTPPTPSPSTPPTPSPS

CCHPRLSLHRPALEDLLLGSEANLTCTLTGLRDASGVTFTWTPSSGKSAVQGPPERDLC

GCYSVSSVLPGCAEPWNHGKTFTCTAAYPESKTPLTATLSKSGNTFRPEVHLLPPPSEEL

```
ALNELVTLTCLARGFSPKDVLVRWLQGSQELPREKYLTWASRQEPSQGTTTFAVTSILR

VAAEDWKKGDTFSCMVGHEALPLAFTQKTIDRLAGKPTHVNVSVVMAEVDGTCY

Human IgA2 constant region, Uniprot: P01877
                                                    SEQ ID NO: 34
ASPTSPKVFPLSLDSTPQDGNVVVACLVQGFFPQEPLSVTWSESGQNVTARNFPPSQDAS

GDLYTTSSQLTLPATQCPDGKSVTCHVKHYTNPSQDVTVPCPVPPPPPCCHPRLSLHRPA

LEDLLLGSEANLTCTLTGLRDASGATFTWTPSSGKSAVQGPPERDLCGCYSVSSVLPGC

AQPWNHGETFTCTAAHPELKTPLTANITKSGNTFRPEVHLLPPPSEELALNELVTLTCLA

RGFSPKDVLVRWLQGSQELPREKYLTWASRQEPSQGTTTFAVTSILRVAAEDWKKGDT

FSCMVGHEALPLAFTQKTIDRMAGKPTHVNVSVVMAEVDGTCY

Human Ig kappa constant region, Uniprot: P01834
                                                    SEQ ID NO: 35
TVAAPSVFIFPPSDEQLKSGTASVVCLLNNFYPREAKVQWKVDNALQSGNSQESVTEQD

SKDSTYSLSSTLTLSKADYEKHKVYACEVTHQGLSSPVTKSFNRGEC
```

In some aspects, the SP263, J45H2L4 and J27H6L4 antibodies comprise a heavy chain constant region that is at least 80% identical to SEQ ID NOS: 27-33 or 34.

In some aspects, the SP263, J45H2L4 and J27H6L4 antibodies comprise a light chain constant region that is at least 80% identical to SEQ ID NO: 35.

In some aspects of the antibodies provided herein, the antibody binds to the epitope bound by SP263, J45H2L4 and J27H6L4.

In some aspects of the antibodies provided herein, the antibody competes with SP263, J45H2L4 and J27H6L4 for binding to PD-L1.

In some aspects of the antibodies provided herein, the antibody contains structural modifications to facilitate rapid binding and cell uptake and/or slow release. In some aspects, the PD-L1 antibody contains a deletion in the CH2 constant heavy chain region of the antibody to facilitate rapid binding and cell uptake and/or slow release. In some aspects, a Fab fragment is used to facilitate rapid binding and cell uptake and/or slow release. In some aspects, a F(ab)'2 fragment is used to facilitate rapid binding and cell uptake and/or slow release.

Processes for Preparing Antibodies and Antibody Fragments

Antibodies, their manufacture and uses are well known and disclosed in, for example, Harlow, E. and Lane, D., *Antibodies: A Laboratory Manual*, Cold Spring Harbor Laboratory Press, Cold Spring Harbor, N.Y., 1999. The antibodies may be generated using standard methods known in the art. Examples of antibodies include (but are not limited to) monoclonal, single chain, and functional fragments of antibodies.

Antibodies may be produced in a range of hosts, for example goats, rabbits, rats, mice, humans, and others. They may be immunized by injection with a target antigen or a fragment or oligopeptide thereof which has immunogenic properties, such as a C-terminal fragment of PD-L1. Depending on the host species, various adjuvants may be used to increase an immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (Bacille Calmette-Guerin) and *Corynebacterium parvum* are particularly useful.

In certain aspects, the antibodies of the present disclosure are polyclonal, i.e., a mixture of plural types of anti-PD-L1 antibodies having different amino acid sequences, e.g., antibodies raised against SEQ ID NO: 1 using techniques known in the art and briefly described below. In one aspect, the polyclonal antibody comprises a mixture of plural types of anti-PD-L1 antibodies having different CDRs. As such, a mixture of cells which produce different antibodies is cultured, and an antibody purified from the resulting culture can be used (see WO 2004/061104).

Monoclonal Antibody Production. Monoclonal antibodies to PD-L1 may be prepared using any technique which provides for the production of antibody molecules by continuous cell lines in culture and in one aspect are prepared using a polypeptide having SEQ ID NO. 1. Such techniques include, but are not limited to, the hybridoma technique (see, e.g., Kohler & Milstein, *Nature* 256: 495-497 (1975)); the trioma technique; the human B-cell hybridoma technique (see, e.g., Kozbor, et al., *Immunol. Today* 4: 72 (1983)) and the EBV hybridoma technique to produce human monoclonal antibodies (see, e.g., Cole, et al., in: MONOCLONAL ANTIBODIES AND CANCER THERAPY, Alan R. Liss, Inc., pp. 77-96 (1985)). Human monoclonal antibodies can be utilized in the practice of the disclosure and can be produced by using human hybridomas (see, e.g., Cote, et al., *Proc. Natl. Acad. Sci.* 80: 2026-2030 (1983)) or by transforming human B-cells with Epstein Barr Virus in vitro (see, e.g., Cole, et al., in: MONOCLONAL ANTIBODIES AND CANCER THERAPY, Alan R. Liss, Inc., pp. 77-96 (1985)). For example, a population of nucleic acids that encode regions of antibodies can be isolated. PCR utilizing primers derived from sequences encoding conserved regions of antibodies is used to amplify sequences encoding portions of antibodies from the population and then reconstruct DNAs encoding antibodies or fragments thereof, such as variable domains, from the amplified sequences. Such amplified sequences also can be fused to DNAs encoding other proteins—e.g., a bacteriophage coat, or a bacterial cell surface protein—for expression and display of the fusion polypeptides on phage or bacteria. Amplified sequences can then be expressed and further selected or isolated based, e.g., on the affinity of the expressed antibody or fragment thereof for an antigen or epitope present on the PD-L1 polypeptide. Alternatively, hybridomas expressing anti-PD-L1 monoclonal antibodies can be prepared by immunizing a subject and then isolating hybridomas from the subject's spleen using routine methods. See, e.g., Milstein et al., (Galfre and Milstein, *Methods Enzymol* 73: 3-46 (1981)). Screening the hybridomas using standard methods will produce monoclonal antibodies of varying specificity (i.e., for different epitopes) and affinity. A selected monoclonal antibody with the desired properties, e.g., PD-L1 binding, can be (i) used as expressed by the hybridoma, (ii) bound to a molecule such as polyethylene glycol (PEG) to alter its properties, or (iii) a cDNA encoding the monoclonal antibody can be isolated, sequenced and manipulated in various ways. In one aspect, the anti-PD-L1 monoclonal antibody is produced by a hybridoma which includes a B cell obtained from a transgenic non-human animal, e.g., a transgenic mouse, having a genome comprising a human heavy chain transgene and a light chain transgene fused to an immortalized cell. Hybridoma techniques include those known in the art and taught in Harlow et al., *Antibodies: A Laboratory Manual* Cold Spring Harbor Laboratory, Cold Spring Harbor, N.Y., 349 (1988); Hammerling et al., *Monoclonal Antibodies And T-Cell Hybridomas,* 563-681 (1981).

Phage Display Technique. As noted above, the antibodies of the present disclosure can be produced through the application of recombinant DNA and phage display technology. For example, anti-PD-L1 antibodies, can be prepared using various phage display methods known in the art. In phage display methods, functional antibody domains are displayed on the surface of a phage particle which carries polynucleotide sequences encoding them. Phage with a desired binding property are selected from a repertoire or combinatorial antibody library (e.g., human or murine) by selecting directly with an antigen, typically an antigen bound or captured to a solid surface or bead. Phage used in these methods are typically filamentous phage including fd and M13 with Fab, $F_v$ or disulfide stabilized $F_v$ antibody domains are recombinantly fused to either the phage gene III or gene VIII protein. In addition, methods can be adapted for the construction of Fab expression libraries (see, e.g., Huse, et al., *Science* 246: 1275-1281, 1989) to allow rapid and effective identification of monoclonal Fab fragments with the desired specificity for a PD-L1 polypeptide, e.g., a polypeptide or derivatives, fragments, analogs or homologs thereof. Other examples of phage display methods that can be used to make the isolated antibodies of the present disclosure include those disclosed in Huston et al., *Proc. Natl. Acad. Sci. U.S.A.,* 85: 5879-5883 (1988); Chaudhary et al., *Proc. Natl. Acad. Sci. U.S.A.,* 87: 1066-1070 (1990); Brinkman et al., *J. Immunol. Methods* 182: 41-50 (1995); Ames et al., *J. Immunol. Methods* 184: 177-186 (1995); Kettleborough et al., *Eur. J. Immunol.* 24: 952-958 (1994); Persic et al., *Gene* 187: 9-18 (1997); Burton et al., *Advances in Immunology* 57: 191-280 (1994); PCT/GB91/01134; WO 90/02809; WO 91/10737; WO 92/01047; WO 92/18619; WO 93/11236; WO 95/15982; WO 95/20401; WO 96/06213; WO 92/01047 (Medical Research Council et al.); WO 97/08320 (Morphosys); WO 92/01047 (CAT/MRC); WO 91/17271 (Affymax); and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743.

Methods useful for displaying polypeptides on the surface of bacteriophage particles by attaching the polypeptides via disulfide bonds have been described by Lohning, U.S. Pat. No. 6,753,136. As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')$_2$ fragments can also be employed using methods known in the art such as those disclosed in WO 92/22324; Mullinax et al., *BioTechniques* 12: 864-869 (1992); Sawai et al., *AJRI* 34: 26-34 (1995); and Better et al., *Science* 240: 1041-1043 (1988).

Generally, hybrid antibodies or hybrid antibody fragments that are cloned into a display vector can be selected against the appropriate antigen in order to identify variants that maintained good binding activity, because the antibody or antibody fragment will be present on the surface of the phage or phagemid particle. See e.g. Barbas III et al., *Phage Display, A Laboratory Manual* (Cold Spring Harbor Laboratory Press, Cold Spring Harbor, N.Y., 2001). However, other vector formats could be used for this process, such as cloning the antibody fragment library into a lytic phage vector (modified T7 or Lambda Zap systems) for selection and/or screening.

Alternate Methods of Antibody Production. Antibodies may also be produced by inducing in vivo production in the lymphocyte population or by screening recombinant immunoglobulin libraries or panels of highly specific binding reagents (Orlandi et al., *PNAS* 86: 3833-3837 (1989); Winter, G. et al., *Nature,* 349: 293-299 (1991)).

Alternatively, techniques for the production of single chain antibodies may be used. Single chain antibodies (scF$_v$s) comprise a heavy chain variable region and a light chain variable region connected with a linker peptide (typically around 5 to 25 amino acids in length). In the scF$_v$, the variable regions of the heavy chain and the light chain may be derived from the same antibody or different antibodies. scF$_v$s may be synthesized using recombinant techniques, for example by expression of a vector encoding the scF$_v$ in a host organism such as *E. coli*. DNA encoding scF$_v$ can be obtained by performing amplification using a partial DNA encoding the entire or a desired amino acid sequence of a DNA selected from a DNA encoding the heavy chain or the variable region of the heavy chain of the above-mentioned antibody and a DNA encoding the light chain or the variable region of the light chain thereof as a template, by PCR using a primer pair that defines both ends thereof, and further performing amplification combining a DNA encoding a polypeptide linker portion and a primer pair that defines both ends thereof, so as to ligate both ends of the linker to the heavy chain and the light chain, respectively. An expression vector containing the DNA encoding scF$_v$ and a host transformed by the expression vector can be obtained according to conventional methods known in the art.

Antigen binding fragments may also be generated, for example the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse et al., *Science,* 256: 1275-1281 (1989)).

Antibody Modifications. The antibodies of the present disclosure may be multimerized to increase the affinity for an antigen. The antibody to be multimerized may be one type of antibody or a plurality of antibodies which recognize a plurality of epitopes of the same antigen. As a method of multimerization of the antibody, binding of the IgG CH3 domain to two scF$_v$ molecules, binding to streptavidin, introduction of a helix-turn-helix motif and the like can be exemplified.

The antibody compositions of the present disclosure may be in the form of a conjugate formed between any of these antibodies and another agent (immunoconjugate). In one aspect, the antibodies of the present disclosure are conjugated to radioactive material. In another aspect, the antibodies of the present disclosure can be bound to various types of molecules such as polyethylene glycol (PEG).

Antibody Screening. Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between PD-L1, or any fragment or oligopeptide thereof and its specific antibody. A two-site, monoclonal-based immunoassay utilizing monoclonal antibodies specific to two non-interfering PD-L1 epitopes may be used, but a competitive binding assay may also be employed (Maddox et al., *J. Exp. Med.,* 158: 1211-1216 (1983)).

Automated immunohistochemistry (IHC) screening of potential anti-PD-L1 antibodies can be performed using a Ventana Medical Systems, Inc (VMSI) Discovery XT and formalin-fixed, paraffin-embedded human tissue on glass slides. Tissue samples first undergo deparaffinization, antigen retrieval, followed by the addition of the potential anti-PD-L1 antibody and a detection antibody. The detection antibody is visualized using a chromogen detection reagent from VMSI. Stained slides are manually screened under a microscope. Samples having a correct primary antibody staining pattern are selected as potential anti-PD-L1 candidates.

Antibody Purification. The antibodies of the present disclosure can be purified to homogeneity. The separation and purification of the antibodies can be performed by employing conventional protein separation and purification methods.

By way of example only, the antibody can be separated and purified by appropriately selecting and combining use of chromatography columns, filters, ultrafiltration, salt precipitation, dialysis, preparative polyacrylamide gel electrophoresis, isoelectric focusing electrophoresis, and the like. *Strategies for Protein Purification and Characterization: A Laboratory Course Manual*, Daniel R. Marshak et al. eds., Cold Spring Harbor Laboratory Press (1996); *Antibodies: A Laboratory Manual.* Ed Harlow and David Lane, Cold Spring Harbor Laboratory (1988).

Examples of chromatography include affinity chromatography, ion exchange chromatography, hydrophobic chromatography, gel filtration chromatography, reverse phase chromatography, and adsorption chromatography. In one aspect, chromatography can be performed by employing liquid chromatography such as HPLC or FPLC.

In one aspect, a Protein A column or a Protein G column may be used in affinity chromatography. Other exemplary columns include a Protein A column, Hyper D, POROS, Sepharose F. F. (Pharmacia) and the like.

Diagnostic and Prognostic Methods

General. The antibodies of the disclosure are useful in methods known in the art relating to the localization and/or quantitation of a PD-L1 polypeptide (e.g., for use in measuring levels of the PD-L1 polypeptide within appropriate physiological samples, for use in diagnostic methods, for use in imaging the polypeptide, and the like). The antibodies of the disclosure are useful in isolating a PD-L1 polypeptide by standard techniques, such as affinity chromatography or immunoprecipitation. A PD-L1 antibody of the disclosure can facilitate the purification of natural PD-L1 polypeptides from biological samples, e.g., mammalian sera or cells as well as recombinantly-produced PD-L1 polypeptides expressed in a host system. Moreover, PD-L1 antibody can be used to detect a PD-L1 polypeptide (e.g., in plasma, a cellular lysate or cell supernatant) in order to evaluate the abundance and pattern of expression of the polypeptide. The PD-L1 antibodies of the disclosure can be used diagnostically to monitor PD-L1 levels in tissue as part of a clinical testing procedure, e.g., to determine the efficacy of a given treatment regimen. The detection can be facilitated by coupling (i.e., physically linking) the PD-L1 antibody of this disclosure to a detectable substance.

Detection of PD-L1 Polypeptide. An exemplary method for detecting the level of PD-L1 polypeptides in a biological sample involves obtaining a biological sample from a subject and contacting the biological sample with a PD-L1 antibody of the present disclosure which is capable of detecting the PD-L1 polypeptides.

In one aspect, the PD-L1 antibodies SP263, J45H2L4 and J27H6L4 or fragments thereof are detectably labeled. The term "labeled", with regard to the antibody is intended to encompass direct labeling of the antibody by coupling (i.e., physically linking) a detectable substance to the antibody, as well as indirect labeling of the antibody by reactivity with another compound that is directly labeled. Non-limiting examples of indirect labeling include detection of a primary antibody using a fluorescently-labeled secondary antibody and end-labeling of a DNA probe with biotin such that it can be detected with fluorescently-labeled streptavidin.

The detection method of this disclosure can be used to detect expression levels of PD-L1 polypeptides in a biological sample in vitro as well as in vivo. In vitro techniques for detection of PD-L1 polypeptides include enzyme linked immunosorbent assays (ELISAs), Western blots, flow cytometry, immunoprecipitations, radioimmunoassay, and immunofluorescence (e.g., IHC). Furthermore, in vivo techniques for detection of PD-L1 polypeptides include introducing into a subject labeled anti-PD-L1 antibody. By way of example only, the antibody can be labeled with a radioactive marker whose presence and location in a subject can be detected by standard imaging techniques. In one aspect, the biological sample contains polypeptide molecules from the test subject.

Immunoassay and Imaging. A PD-L1 antibody of the present disclosure can be used to assay PD-L1 polypeptide levels in a biological sample (e.g., a cell or tissue sample) using antibody-based techniques. For example, protein expression in tissues can be studied with classical immunohistochemical (IHC) staining methods. Jalkanen, M. et al., *J. Cell. Biol.* 101: 976-985 (1985); Jalkanen, M. et al., *J. Cell. Biol.* 105: 3087-3096 (1987). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes or other radioactive agents, such as iodine ($^{125}$I, $^{121}$I, $^{131}$I), carbon ($^{14}$C), sulfur ($^{35}$S), tritium ($^{3}$H), indium ($^{112}$In), and technetium ($^{99}$mTc), and fluorescent labels, such as fluorescein and rhodamine, and biotin.

In addition to assaying PD-L1 polypeptide levels in a biological sample, PD-L1 polypeptide levels can also be detected in vivo by imaging. Labels that can be incorporated with anti-PD-L1 antibodies for in vivo imaging of PD-L1 polypeptide levels include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which can be incorporated into the PD-L1 antibody by labeling of nutrients for the relevant $scF_v$ clone.

A PD-L1 antibody which has been labeled with an appropriate detectable imaging moiety, such as a radioisotope (e.g., $^{131}$I, $^{112}$In, $^{99}$mTc), a radio-opaque substance, or a material detectable by nuclear magnetic resonance, is introduced (e.g., parenterally, subcutaneously, or intraperitoneally) into the subject. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$mTc. The labeled PD-L1 antibody will then preferentially accumulate at the location of cells which contain the specific target polypeptide. For example, in vivo tumor imaging is described in S. W. Burchiel et al., *Tumor Imaging: The Radiochemical Detection of Cancer* 13 (1982).

In some aspects, PD-L1 antibodies containing structural modifications that facilitate rapid binding and cell uptake and/or slow release are useful in in vivo imaging detection methods. In some aspects, the PD-L1 antibody contains a deletion in the CH2 constant heavy chain region of the antibody to facilitate rapid binding and cell uptake and/or slow release. In some aspects, a Fab fragment is used to facilitate rapid binding and cell uptake and/or slow release. In some aspects, a F(ab)'2 fragment is used to facilitate rapid binding and cell uptake and/or slow release.

Diagnostic Uses of PD-L1 Antibodies. The PD-L1 antibody compositions of the disclosure are useful in diagnostic and prognostic methods. As such, the present disclosure provides methods for using the antibodies of the disclosure useful in the diagnosis of PD-L1-related medical conditions in a subject. Antibodies of the disclosure may be selected such that they have a high level of epitope binding specificity and high binding affinity to the PD-L1 polypeptide. In general, the higher the binding affinity of an antibody, the more stringent wash conditions can be performed in an immunoassay to remove nonspecifically bound material without removing the target polypeptide. Accordingly, PD-L1 antibodies of the disclosure useful in diagnostic assays usually have binding affinities of at least $10^{-6}$, $10^{-7}$, $10^{-8}$, $10^{-9}$, $10^{-10}$, $10^{-11}$, or $10^{-12}$ M. In certain aspects, PD-L1 antibodies used as diagnostic reagents have a sufficient kinetic on-rate to reach equilibrium under standard conditions in at least 12 hours, at least 5 hours, at least 1 hour, or at least 30 minutes.

Some methods of the disclosure employ polyclonal preparations of anti-PD-L1 antibodies and anti-PD-L1 antibody compositions of the disclosure as diagnostic reagents, and other methods employ monoclonal isolates. In methods employing polyclonal human anti-PD-L1 antibodies prepared in accordance with the methods described above, the preparation typically contains an assortment of PD-L1 antibodies, e.g., antibodies, with different epitope specificities to the target polypeptide. The monoclonal anti-PD-L1 antibodies of the present disclosure are useful for detecting a single antigen in the presence or potential presence of closely related antigens.

The PD-L1 antibodies of the present disclosure can be used as diagnostic reagents for any kind of biological sample. In one aspect, the PD-L1 antibodies disclosed herein are useful as diagnostic reagents for human biological samples. PD-L1 antibodies can be used to detect PD-L1 polypeptides in a variety of standard assay formats. Such formats include immunoprecipitation, Western blotting, ELISA, radioimmunoassay, flow cytometry, IHC and immunometric assays. See Harlow & Lane, *Antibodies, A Laboratory Manual* (Cold Spring Harbor Publications, New York, 1988); U.S. Pat. Nos. 3,791,932; 3,839,153; 3,850, 752; 3,879,262; 4,034,074, 3,791,932; 3,817,837; 3,839, 153; 3,850,752; 3,850,578; 3,853,987; 3,867,517; 3,879, 262; 3,901,654; 3,935,074; 3,984,533; 3,996,345; 4,034, 074; and 4,098,876. Biological samples can be obtained from any tissue (including biopsies), cell or body fluid of a subject.

Prognostic Uses of PD-L1 Antibodies. The disclosure also provides for prognostic (or predictive) assays for determining whether a subject is at risk of developing a medical disease or condition associated with increased PD-L1 polypeptide expression or activity (e.g., detection of a precancerous cell). Such assays can be used for prognostic or predictive purpose to thereby prophylactically treat an individual prior to the onset of a medical disease or condition characterized by or associated with PD-L1 polypeptide expression.

Another aspect of the disclosure provides methods for determining PD-L1 expression in a subject to thereby select appropriate therapeutic or prophylactic compounds for that subject.

Alternatively, the prognostic assays can be utilized to identify a subject having or at risk for developing bladder transitional cell carcinoma, lung adenocarcinoma, breast ductal carcinoma, Hodgkin's lymphoma, pancreas adenocarcinoma, prostate adenocarcinoma, cervical squamous cell carcinoma, skin squamous cell carcinoma, and non-small cell lung cancer. Thus, the disclosure provides a method for identifying a disease or condition associated with increased PD-L1 polypeptide expression levels in which a test sample is obtained from a subject and the PD-L1 polypeptide detected, wherein the presence of increased levels of PD-L1 polypeptides compared to a control sample is predictive for a subject having or at risk of developing a disease or condition associated with increased PD-L1 polypeptide expression levels. In some aspects, the disease or condition associated with increased PD-L1 polypeptide expression levels is selected from the group consisting of bladder transitional cell carcinoma, lung adenocarcinoma, breast ductal carcinoma, Hodgkin's lymphoma, pancreas adenocarcinoma, prostate adenocarcinoma, cervical squamous cell carcinoma, skin squamous cell carcinoma, and non-small cell lung cancer.

In, another aspect, the disclosure provides methods for determining whether a subject can be effectively treated with a compound for a disorder or condition associated with increased PD-L1 polypeptide expression wherein a biological sample is obtained from the subject and the PD-L1 polypeptide is detected using the PD-L1 antibody. The expression level of the PD-L1 polypeptide in the biological sample obtained from the subject is determined and compared with the PD-L1 expression levels found in a biological sample obtained from a subject who is free of the disease. Elevated levels of the PD-L1 polypeptide in the sample obtained from the subject suspected of having the disease or condition compared with the sample obtained from the healthy subject is indicative of the PD-L1-associated disease or condition in the subject being tested.

There are a number of disease states in which the elevated expression level of PD-L1 polypeptides is known to be indicative of whether a subject with the disease is likely to respond to a particular type of therapy or treatment. Thus, the method of detecting a PD-L1 polypeptide in a biological sample can be used as a method of prognosis, e.g., to evaluate the likelihood that the subject will respond to the therapy or treatment. The level of the PD-L1 polypeptide in a suitable tissue or body fluid sample from the subject is determined and compared with a suitable control, e.g., the level in subjects with the same disease but who have responded favorably to the treatment.

In one aspect, the present disclosure provides for methods of monitoring the influence of agents (e.g., drugs, compounds, or small molecules) on the expression of PD-L1 polypeptides. Such assays can be applied in basic drug screening and in clinical trials. For example, the effectiveness of an agent to decrease PD-L1 polypeptide levels can be monitored in clinical trials of subjects exhibiting elevated expression of PD-L1, e.g., patients diagnosed with cancer. An agent that affects the expression of PD-L1 polypeptides can be identified by administering the agent and observing a response. In this way, the expression pattern of the PD-L1 polypeptide can serve as a marker, indicative of the physiological response of the subject to the agent. Accordingly, this response state may be determined before, and at various points during, treatment of the subject with the agent.

In one aspect, the present disclosure provides for methods of monitoring or predicting the efficacy of therapeutic agents that target the PD-L1:PD-1 pathway. In one aspect, the agent is a therapeutic monoclonal antibody which specifically inhibits PD-1 or PD-L1, thereby resulting in a reduction of the activity or expression of PD-1 or PD-L1. Non-limiting examples of therapeutic monoclonal antibodies that specifically target PD-1 or PD-L1 can be found in Brahmer et al., *N Engl J Med.* 366(26): 2455-2465 (2012) (describing the anti-PD-L1 antibody BMS-936559); Topalian et al., *N Engl J Med.* 366(26): 2443-2454 (2012) (describing the anti-PD-1 antibody BMS-936558); MPDL3280A (anti-PD-L1 monoclonal antibody, Genentech, San Francisco Calif.); MEDI4736 (anti-PD-L1 monoclonal antibody, AstraZeneca); MSB0010718C (anti-PD-L1 monoclonal antibody, Merck Serono, Germany); and MK-3475 (anti-PD-1 monoclonal antibody, Merck, Germany).

Automated Embodiments. A person of ordinary skill in the art will appreciate that aspects of the methods for using the PD-L1 antibodies disclosed herein can be automated. Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. published application Nos. 20030211630 and 20040052685, each of which is incorporated herein by reference. Particular aspects of PD-L1 staining procedures can be conducted using various automated processes.

Kits

As set forth herein, the disclosure provides diagnostic methods for determining the expression level of PD-L1. In one particular aspect, the disclosure provides kits for performing these methods as well as instructions for carrying out the methods of this disclosure such as collecting tissue and/or performing the screen, and/or analyzing the results.

The kit comprises, or alternatively consists essentially of, or yet further consists of, a PD-L1 antibody composition (e.g., monoclonal antibodies) of the present disclosure, and instructions for use. The kits are useful for detecting the presence of PD-L1 polypeptides in a biological sample e.g., any body fluid including, but not limited to, e.g., sputum, serum, plasma, lymph, cystic fluid, urine, stool, cerebrospinal fluid, acitic fluid or blood and including biopsy samples of body tissue. The test samples may also be a tumor cell, a normal cell adjacent to a tumor, a normal cell corresponding to the tumor tissue type, a blood cell, a peripheral blood lymphocyte, or combinations thereof. The test sample used in the above-described method will vary based on the assay format, nature of the detection method and the tissues, cells or extracts used as the sample to be assayed. Methods for preparing protein extracts or membrane extracts of cells are known in the art and can be readily adapted in order to obtain a sample which is compatible with the system utilized.

In some aspects, the kit can comprise: one or more PD-L1 antibodies capable of binding a PD-L1 polypeptide in a biological sample (e.g., an antibody or antigen-binding fragment thereof having the same antigen-binding specificity of PD-L1 antibodies SP263, J45H2L4 and J27H6L4); means for determining the amount of the PD-L1 polypeptide in the sample; and means for comparing the amount of the PD-L1 polypeptide in the sample with a standard. One or more of the PD-L1 antibodies may be labeled. The kit components, (e.g., reagents) can be packaged in a suitable container. The kit can further comprise instructions for using the kit to detect the PD-L1 polypeptides. In certain aspects, the kit comprises a first antibody, e.g., attached to a solid support, which binds to a PD-L1 polypeptide; and, optionally; 2) a second, different antibody which binds to either the PD-L1 polypeptide or the first antibody and is conjugated to a detectable label.

The kit can also comprise, e.g., a buffering agent, a preservative or a protein-stabilizing agent. The kit can further comprise components necessary for detecting the detectable-label, e.g., an enzyme or a substrate. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the disclosure may contain a written product on or in the kit container. The written product describes how to use the reagents contained in the kit.

As amenable, these suggested kit components may be packaged in a manner customary for use by those of skill in the art. For example, these suggested kit components may be provided in solution or as a liquid dispersion or the like.

EXAMPLES

Example 1

Rabbit Monoclonal Antibody Generation

FIG. 1 illustrates the overall procedure used to create PD-L1 monoclonal antibodies using a rabbit host. The anti-PD-L1 rabbit monoclonal primary antibodies were directed against the sequence CGIQDTNSKKQSDTH-LEET (SEQ ID NO: 1), which represents amino acid residues 272-290 of human PD-L1. Thus, the resulting antibodies would target the C-terminal cytoplasmic region of human PD-L1 much like the E1L3N® anti-PD-L1 antibody (Cell Signaling Technology, MA).

The 19-amino acid peptide was synthesized and covalently conjugated to a keyhole limpet haemocyanin (KLH) carrier protein. New Zealand white rabbits were immunized with KLH-conjugated peptide emulsified with complete Freund's adjuvant followed by a series of booster doses of immunogen emulsified with incomplete Freund's adjuvant.

The rabbit that generated a IHC positive polyclonal antibody was selected for further monoclonal development. For IHC testing, standard OptiView DAB kit protocol was used on BenchMark Ultra platform (Ventana Medical System) after StdCC1 cell conditioning. Briefly, primary antibody was incubated for 16 min at 37° C., followed by incubation with a haptenated secondary antibody that reacts with the primary antibody. Anti-hapten HRP multimer was subsequently added, which reacts with the haptenated secondary antibody. Lastly, the target antigen was detected using a chromogenic substrate (DAB).

For ELISA, antibody-expressing cells were isolated and screened via standard direct enzyme-linked immunoabsorbant assay (ELISA) for reactivity to the sequence CGIQDTNSKKQSDTHLEET (SEQ ID NO: 1) (See *Antibodies: A Laboratory Manual*, page 661, Second edition) and by IHC assays on control placental tissue blocks. Once IHC positive antibody producing cells were identified, the cDNAs coding for the antibody heavy chain and light chain were isolated and cloned using standard recombinant techniques. Monoclonal antibodies were subsequently produced by co-transfecting the cloned heavy and light chain cDNAs and the functionality of the resulting antibodies was verified by IHC. Rabbit anti-human PD-L1 monoclonal antibodies with the best specificity, i.e., SP263, J45H2L4 and J27H6L4 were selected and subsequently purified through a Protein A column. The CDR regions of the SP263, J45H2L4 and J27H6L4 antibodies are provided in Table 1:

TABLE 1

| | HC | | |
|---|---|---|---|
| Antibody | CDR1 | CDR2 | CDR3 |
| SP263 | NHAIS (SEQ ID NO: 14) | TINSDTHTYYATWPKG (SEQ ID NO: 15) | RIFSSSNI (SEQ ID NO: 16) |
| J45H2L4 | SNAIS (SEQ ID NO: 19) | TINSDSHIYSATWAKG (SEQ ID NO: 20) | RLFSSTNI (SEQ ID NO: 21) |
| J27H6L4 | SHAIS (SEQ ID NO: 24) | TINSDSHTYYATWAKG (SEQ ID NO: 25) | RIFSSSNI (SEQ ID NO: 16) |

| | LC | | |
|---|---|---|---|
| Antibody | CDR1 | CDR2 | CDR3 |
| SP263 | QASQSIYNNNWLS (SEQ ID NO: 17) | LASTLAS (SEQ ID NO: 12) | IGGESSNNDGIA (SEQ ID NO: 18) |
| J45H2L4 | QASQSIYKDNWLS (SEQ ID NO: 22) | LASTLAS (SEQ ID NO: 12) | LGGESSSDDGIA (SEQ ID NO: 23) |
| J27H6L4 | QASQSIYNNNWLS (SEQ ID NO: 17) | LASTLAS (SEQ ID NO: 12) | IGGESSNTDGIA (SEQ ID NO: 26) |

The amino acid sequences of CDR1, CDR2 and CDR3 regions of the anti-PD-L1 antibodies SP263, J45H2L4 and J27H6L4 conform with the consensus sequences provided below:

Heavy chain CDR1 consensus sequence is $X_{10}X_{11}AIS$ (SEQ ID NO: 8), wherein $X_{10}$ is N or S, and $X_{11}$ is H or N.

Heavy chain CDR2 consensus sequence is TINSDX$_6$HX$_7$YX$_8$ATWX$_9$KG (SEQ ID NO: 9), wherein $X_6$ is T or S, $X_7$ is T or I, $X_8$ is Y or S, and $X_9$ is P or A.

Heavy chain CDR3 consensus sequence is RX$_1$FSSX$_2$NI (SEQ ID NO: 10), wherein $X_1$ is I or L, and $X_2$ is S or T.

Light chain CDR1 consensus sequence is QASQSIYX$_{12}$X$_{13}$NWLS (SEQ ID NO: 11), wherein $X_{12}$ is N or K and $X_{13}$ is N or D.

Light chain CDR3 consensus sequence is X$_3$GGESSX$_4$X$_5$DGIA (SEQ ID NO: 13), wherein $X_3$ is L or I, $X_4$ is N or S, and $X_5$ is N, T or D.

Light chain CDR2 sequence is LASTLAS (SEQ ID NO: 12).

The HC immunoglobulin variable domain sequences and LC immunoglobulin variable domain sequences of the SP263, J45H2L4 and J27H6L4 antibodies are provided below:

```
SP263 HC immunoglobulin variable domain sequence:
                                        (SEQ ID NO: 2)
QSLEESGGRLVTPGTPLTLTCTASGFSLSNHAISWVRQAPGKGLEWIGT

INSDTHTYYATWPKGRFTISKTSSTTVDLKMTSPTTEDTATYFCARRIF

SSSNIWGPGTLVTVSS

SP263 LC immunoglobulin variable domain sequence
(kappa):
                                        (SEQ ID NO: 3)
AIVMTQTSSPVSAVVGGTVAINCQASQSIYNNNWLSWFQQKPGQPPKLL

IYLASTLASGVPSRFKGSGSGTQFTLTISDVVCDDAATYYCIGGESSNN

DGIAFGGGTEVVVK

J45H2L4 HC immunoglobulin variable domain
sequence:
                                        (SEQ ID NO: 4)
QSLEESGGRLVTPGTPLTLTCTASGFSLSSNAISWVRQAPGKGLEWIGT

INSDSHIYSATWAKGRFTISKTSTAVDLKMTSPTTEDTATYFCAGRLFS

STNIWGPGTLVTVSS

J45H2L4 LC immunoglobulin variable domain
sequence (kappa):
                                        (SEQ ID NO: 5)
VMTQTSSPVSAAVGGTVTINCQASQSIYKDNWLSWFQQKPGQPPKLLIY

LASTLASGVPSRFKGSGSGTQFTLTISDVVCDDAATYYCLGGESSSDDG

IAFGGGTEVVVK

J27H6L4 HC immunoglobulin variable domain
sequence:
                                        (SEQ ID NO: 6)
QSLEESGGRLVTPGTPLTLTCTVSGFSLSSHAISWVRQAPGKGLEWIGT

INSDSHTYYATWAKGRETSSKTSTTVDLKLTSPTTEDTATYFCARRIFS

SSNIWGPGTLVTVSS

J27H6L4 LC immunoglobulin variable domain
sequence (kappa):
                                        (SEQ ID NO: 7)
VMTQTSSPVSAAVGGTVTINCQASQSIYNNNWLSWFQQKPGQPPKLLIY

LASTLASGVPSRFKGSGSGTQSTLTISDVVCDDAATYYCIGGESSNTDG

IAFGGGTEVVVE
```

Example 2

Target Specificity of Anti-PD-L1 Antibodies

Rabbit anti-human PD-L1 monoclonal antibodies SP263, J45H2L4 and J27H6L4 were applied onto formalin-fixed paraffin embedded (FFPE) tissue samples to assess the staining patterns of these antibodies. Tissue samples include placenta (positive control), stomach (negative control) and colon. Immunohistochemistry was performed on BenchMark Ultra (Ventana Medical System) using StdCC1 cell conditioning and standard Opt iView DAB detection protocol. Each primary antibody was incubated at 0.9 µg/ml for 16 min.

Figures 4A, 4B, 4C, 4D, 4E, 4F, 4G, 4H, 4I:
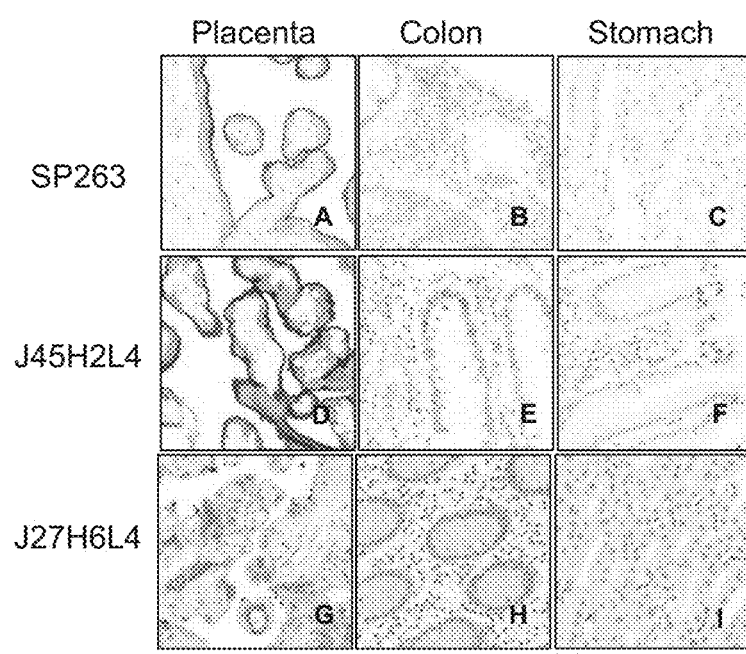
FIG. 4A is an image showing the results of IHC on a FFPE placental tissue section using anti-PD-L1 antibody SP263.
FIG. 4B is an image showing the results of IHC on a FFPE colon tissue section using anti-PD-L1 antibody SP263.
FIG. 4C is an image showing the results of IHC on a FFPE stomach tissue section using anti-PD-L1 antibody SP263.
FIG. 4D is an image showing the results of IHC on a FFPE placenta tissue section using anti-PD-L1 antibody clone J45H2L4.
FIG. 4E is an image showing the results of IHC on a FFPE colon tissue section using anti-PD-L1 antibody clone J45H2L4. Non-specific nuclear staining is seen.
FIG. 4F is an image showing the results of IHC on a FFPE stomach tissue section using anti-PD-L1 antibody clone J45H2L4. Non-specific nuclear staining is seen.
FIG. 4G is an image showing the results of IHC on a FFPE placenta tissue section using anti-PD-L1 antibody clone J27H6L4. Weak staining is seen in placental trophoblasts.
FIG. 4H is an image showing the results of IHC on a FFPE colon tissue section using anti-PD-L1 antibody clone J27H6L4.
FIG. 4I is an image showing the results of IHC on a FFPE stomach tissue section using anti-PD-L1 antibody clone J27H6L4.

As shown in FIG. 4G, the J27H6L4 anti-PD-L1 antibody exhibited weak staining in placental trophoblasts and no staining in colon and stomach tissue (FIGS. 4H-4I). In contrast, the J45H2L4 anti-PD-L1 antibody generated the strongest signal in placental trophoblasts. See FIG. 4D. However, J45H2L4 also exhibited significant background staining, as demonstrated by the non-specific nuclear staining in colon and stomach tissue (FIGS. 4E and 4F). As shown in FIG. 4A, the SP263 antibody yielded a strong signal in the cell membranes of the placental syncytiotrophoblasts and little to no background staining in the control stomach and colon tissues (FIGS. 4B-4C). The SP263 anti-PD-L1 antibody was selected for further characterization in light of its favorable immunostaining properties.

SP263 anti-PD-L1 antibody was applied onto FFPE placental, tonsil, Hodgkin's lymphoma, and lung squamous cell carcinoma tissue samples. Each of these four tissues is known to exhibit high levels of membrane-associated PD-L1 expression. Immunohistochemistry was performed on BenchMark Ultra (Ventana Medical System) using StdCC1 cell conditioning and standard Opt iView DAB detection protocol. The SP263 was incubated at 0.9 µg/ml for 16 min.

As shown in FIGS. 2A-2D, incubation with the SP263 antibody yielded robust membrane-associated PD-L1 staining in placental, tonsil, Hodgkin's lymphoma, and lung squamous cell carcinoma tissue samples, which is consistent with the PD-L1 expression patterns described in Brown et al., *J. Immunol.* 170:1257-1266 (2003). Thus, these results demonstrate that the PD-L1 antibodies of the present disclosure are useful in methods for detecting PD-L1 polypeptide levels in a biological sample. The tumor cells from Hodgkin's lymphoma and lung squamous cell carcinoma in FIGS. 2C and 2D demonstrated positive PD-L1 staining, while the stromal cells surrounding the PD-L1 positive cancer cells served as negative control cells, which prove the specificity of the PD-L1 antibody. Thus, the results demonstrate that the PD-L1 antibodies of the present disclosure are useful in methods for detecting cancerous cells in a subject.

Example 3

Characterization of the SP263 Anti-human PD-L1 Antibody

Western blot analysis was used to assess the binding specificity of the SP263 anti-PD-L1 antibody in biological samples. Cell lysates from a NIH H820 lung adenocarcinoma cell line (positive control), a HEK293 cell line, a Calu-3 lung adenocarcinoma cell line (negative control), a ZR75-1 human breast carcinoma cell line (negative control), a MCF7 human breast carcinoma cell line (negative control), and a T47D human breast carcinoma cell line (negative control) were fractionated by SDS-PAGE and was subjected to western blotting with the SP263 anti-PD-L1 antibody using standard techniques (see OptiView DAB detection protocol).

Figure 3:
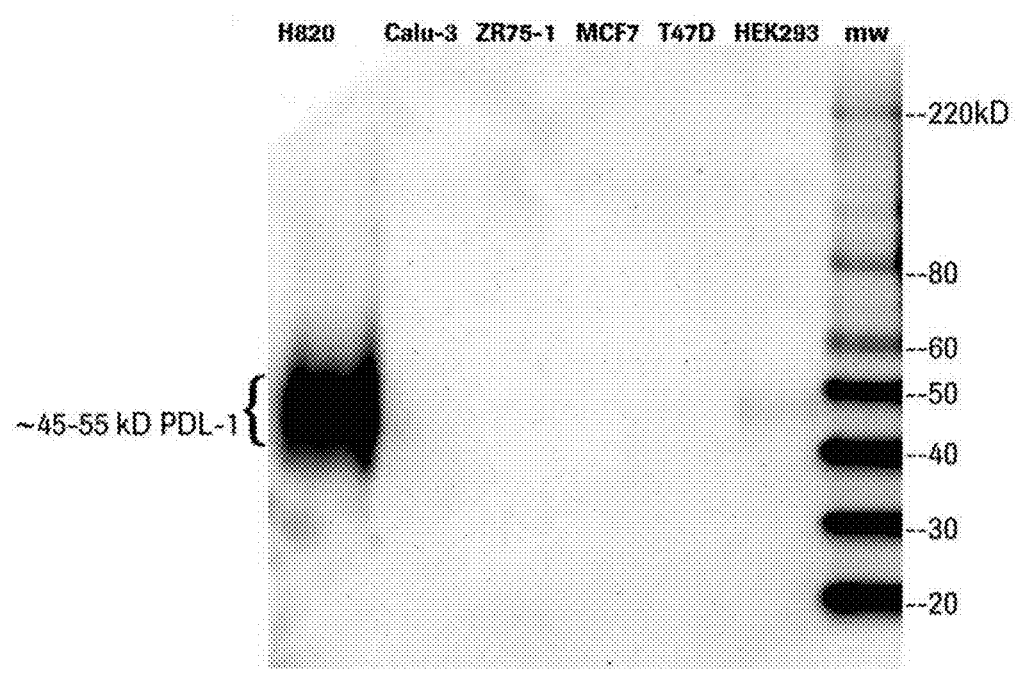
FIG. 3 is a Western blot showing PD-L1 expression in cell lysates from a NIH H820 lung adenocarcinoma cell line (high expression), a HEK293 cell line (weak expression), a Calu-3 lung adenocarcinoma cell line (negative control), a ZR75-1 human breast carcinoma cell line (negative control), a MCF7 human breast carcinoma cell line (negative control), and a T47D human breast carcinoma cell line (negative control) using anti-PD-L1 antibody SP263.

As shown in FIG. 3, SP263 bound a ~45-55 kDa protein which corresponds to human PD-L1 protein. The 45-55 kDa PD-L1 protein was detected in NIH H820 lung adenocarcinoma cells (which are known to exhibit elevated levels of PD-L1), and was absent in all 4 negative controls. Further, in addition to specifically binding human PD-L1, these results show that the SP263 antibody is capable of detecting the low endogenous levels of PD-L1 in HEK293 cells (which are derived from kidney). The results of the Western blot assay thus bolster the IHC results shown in FIG. 2.

Figure 10:
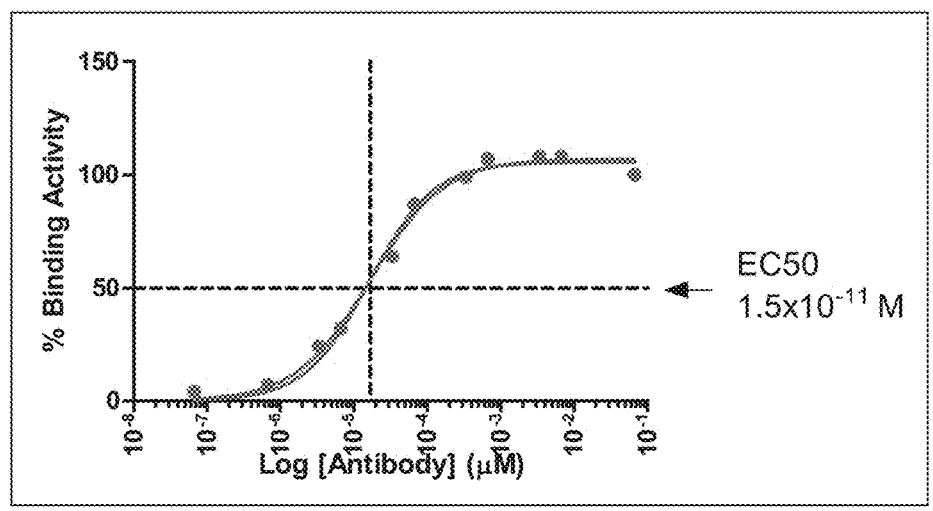
FIG. 10 shows the results of an ELISA assay involving SP263 binding to immobilized peptide immunogen (PD-L1 aa 272-290).

ELISA studies were performed with the SP263 antibody to evaluate binding to the immobilized peptide immunogen (human PD-L1 aa272-290). A summary of the results are shown in FIG. 10. The $EC_{50}$ of the SP263 antibody is $1.5 \times 10^{-11}$ M, thus demonstrating the high potency of the antibody with respect to binding the PD-L1 epitope.

Example 4

SP263 Anti-human PD-L1 Antibody Exhibits Superior Binding Specificity Compared to E1L3N® Anti-PD-L1 Antibody The E1L3N® antibody (Cell Signaling Technology, MA) is a commercially available rabbit anti-human PD-L1 monoclonal antibody that is recognized for its improved binding properties (specificity and sensitivity), thereby aiding in the detection of human-PD-L1 polypeptides in biological samples (e.g., tissue biopsies). The SP263 and E1L3N® antibodies both target epitopes near the C-terminal region of human PD-L1 and thus bind to the intracellular domain of PD-L1.

SP263 anti-PD-L1 antibody (0.44 µg/ml unless otherwise specified) was applied onto FFPE stomach, nerve, kidney, bladder transitional cell carcinoma, breast ductal carcinoma and lung squamous cell carcinoma tissue samples Immunohistochemistry was performed on BenchMark Ultra (Ventana Medical System) using StdCC1 cell conditioning with Opt iView detection kit. Corresponding IHC experiments with the E1L3N® antibody were conducted in accordance with the manufacturer's protocols.

Figures 6A, 6T:
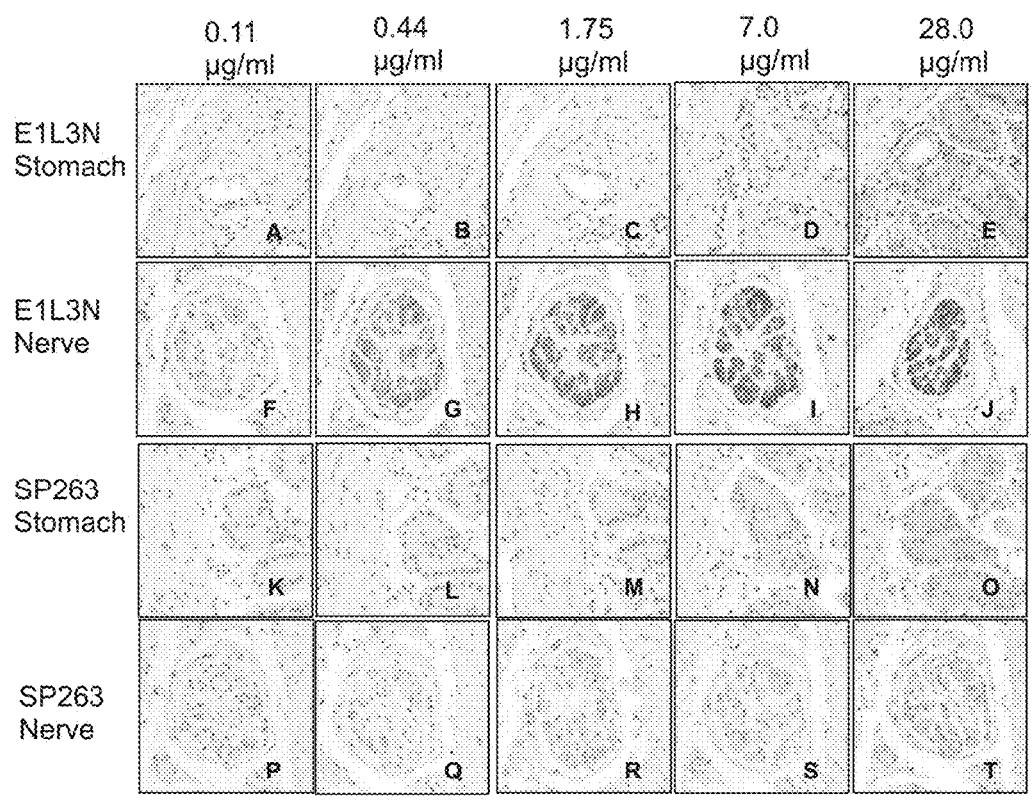
FIG. 6A is an image showing the results of IHC on a FFPE stomach epithelium tissue section using anti-PD-L1 antibody E1L3N at a concentration of 0.11 µg/ml.
FIG. 6T is an image showing the results of IHC on a FFPE nerve tissue section using anti-PD-L1 antibody SP263 at a concentration of 28.0 µg/ml.
Figures 7A, 7B, 7C, 7D, 7E, 7F, 7G, 7H, 7I, 7J:
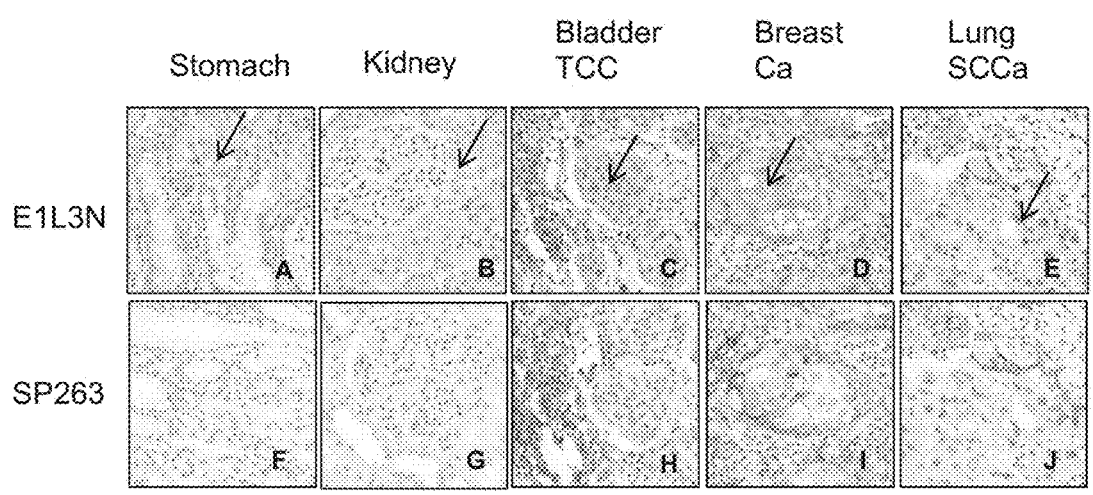
FIG. 7A is an image showing the results of IHC on a FFPE stomach epithelium tissue section using anti-PD-L1 antibody E1L3N.
FIG. 7B is an image showing the results of IHC on a FFPE kidney tissue section using anti-PD-L1 antibody E1L3N.
FIG. 7C is an image showing the results of IHC on a FFPE bladder transitional cell carcinoma (TCC) tissue section using anti-PD-L1 antibody E1L3N.
FIG. 7D is an image showing the results of IHC on a FFPE breast ductal carcinoma (Ca) tissue section using anti-PD-L1 antibody E1L3N.
FIG. 7E is an image showing the results of IHC on a FFPE lung squamous cell carcinoma tissue section using anti-PD-L1 antibody E1L3N.
FIG. 7F is an image showing the results of IHC on a FFPE stomach epithelium tissue section using anti-PD-L1 antibody SP263.
FIG. 7G is an image showing the results of IHC on a FFPE kidney tissue section using anti-PD-L1 antibody SP263.
FIG. 7H is an image showing the results of IHC on a FFPE bladder transitional cell carcinoma (TCC) tissue section using anti-PD-L1 antibody SP263.
FIG. 7I is an image showing the results of IHC on a FFPE breast ductal carcinoma (Ca) tissue section using anti-PD-L1 antibody SP263.
FIG. 7J is an image showing the results of IHC on a FFPE lung squamous cell carcinoma tissue section using anti-PD-L1 antibody SP263.
Figures 8A, 8B, 8C, 8D, 8E, 8F, 8G, 8H, 8I, 8J, 8K, 8L:
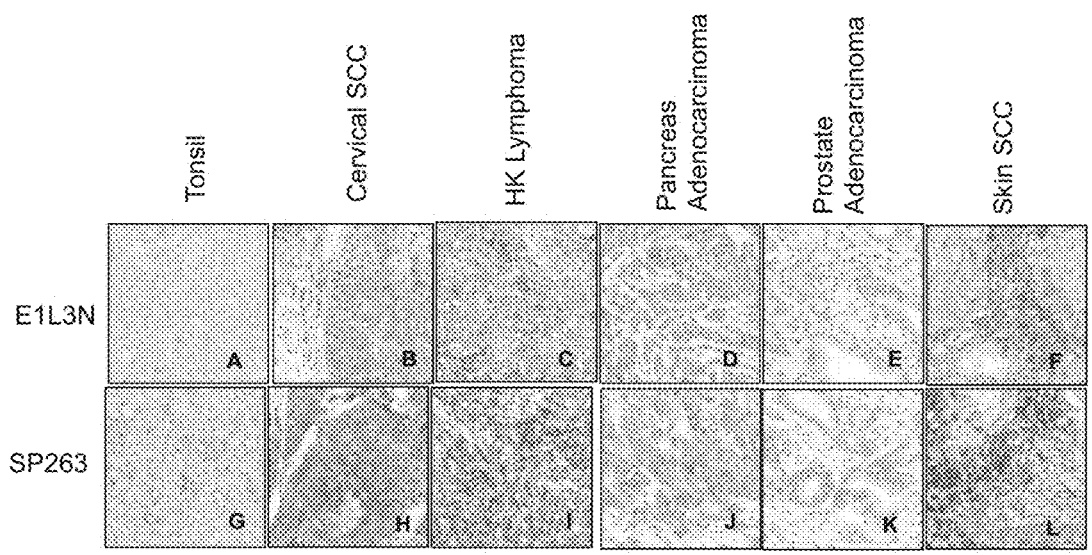
FIG. 8A is an image showing the results of IHC on a FFPE tonsil tissue section using anti-PD-L1 antibody E1L3N.
FIG. 8B is an image showing the results of IHC on a FFPE cervical squamous cell carcinoma (SCC) tissue section using anti-PD-L1 antibody E1L3N.
FIG. 8C is an image showing the results of IHC on a FFPE Hodgkin Lymphoma (HK lymphoma) tissue section using anti-PD-L1 antibody E1L3N.
FIG. 8D is an image showing the results of IHC on a FFPE pancreatic adenocarcinoma tissue section using anti-PD-L1 antibody E1L3N.
FIG. 8E is an image showing the results of IHC on a FFPE prostate adenocarcinoma tissue section using anti-PD-L1 antibody E1L3N.
FIG. 8F is an image showing the results of IHC on a FFPE skin SCC tissue section using anti-PD-L1 antibody E1L3N.
FIG. 8G is an image showing the results of IHC on a FFPE tonsil tissue section using anti-PD-L1 antibody SP263.
FIG. 8H is an image showing the results of IHC on a FFPE cervical squamous cell carcinoma (SCC) tissue section using anti-PD-L1 antibody SP263.
FIG. 8I is an image showing the results of IHC on a FFPE Hodgkin Lymphoma (HK lymphoma) tissue section using anti-PD-L1 antibody SP263.
FIG. 8J is an image showing the results of IHC on a FFPE pancreatic adenocarcinoma tissue section using anti-PD-L1 antibody SP263.
FIG. 8K is an image showing the results of IHC on a FFPE prostate adenocarcinoma tissue section using anti-PD-L1 antibody SP263.
FIG. 8L is an image showing the results of IHC on a FFPE skin SCC tissue section using anti-PD-L1 antibody SP263.
Figures 9A, 9B, 9C, 9D, 9E, 9F, 9G, 9H, 9I, 9J:
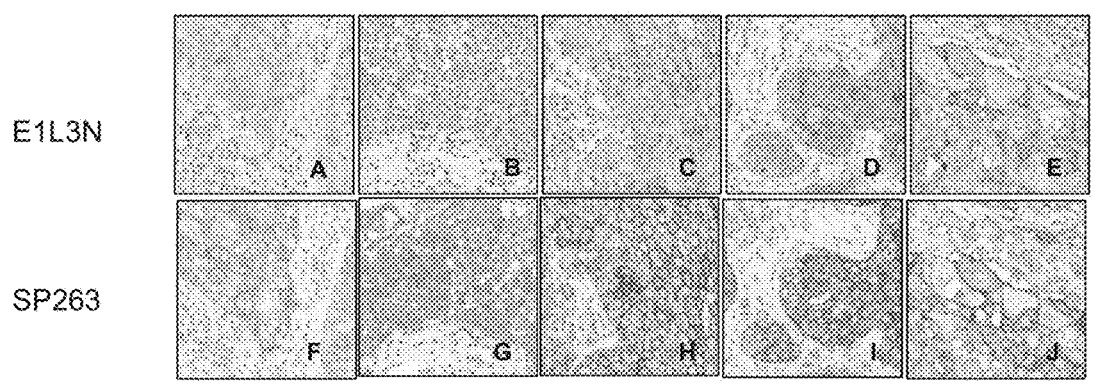
FIGS. 9A-9E show the results of IHC on FFPE tissue sections from NSCLC patients using the anti-PD-L1 antibody E1L3N.
FIGS. 9F-9J show the results of IHC on FFPE tissue sections from NSCLC patients using anti-PD-L1 antibody SP263.

As shown in FIG. 6, both SP263 and E1L3N® were tested at different concentrations. FIGS. 6F-6J show that E1L3N® exhibited significant background staining in FFPE nerve tissue at concentrations as low as 0.44 µg/ml (FIG. 6G). In contrast, the SP263 antibody exhibited comparatively little background staining in FFPE nerve tissue at all tested concentrations (FIGS. 6P-6T). For example, the intensity of the background staining in FFPE nerve tissue with the SP263 antibody at 28 µg/ml was similar to that observed with the E1L3N® antibody at 0.11 µg/ml (Compare FIG. 6T with FIG. 6F). Further, the background staining in FFPE stomach tissue with the SP263 antibody at 28 µg/ml was weaker compared to that observed with the E1L3N® at the same concentration (Compare FIG. 6O to FIG. 6E).

FIGS. 7A-7E demonstrate that the E1L3N® antibody shows non-specific nuclear or cytoplasmic staining in stomach, kidney, bladder transitional cell carcinoma, breast ductal carcinoma and lung squamous cell carcinoma tissue samples (See arrows in FIGS. 7A-7E). In contrast, no non-specific staining was observed with the SP263 antibody in any of the corresponding tissue samples (See FIGS. 7F-7J), which comports with the membranous PD-L1 expression described in Ghebeh et al., *Neoplasia* 8(3):190-198 (2006). Further, SP263 exhibited robust staining in bladder transitional cell carcinoma, breast ductal carcinoma and lung squamous cell carcinoma tissue samples and no staining in the negative control, i.e., the stomach tissue. See FIGS. 7F and 7H-J. These results demonstrate that the PD-L1 antibodies of the present disclosure exhibit superior specificity over other commercially available PD-L1 antibodies that target similar epitopes at the C-terminal region of human PD-L1. Thus, the PD-L1 antibodies of the present disclosure are useful in methods for detecting PD-L1 polypeptide levels in a biological sample and diagnosing cancer in a subject.

Example 5

SP263 Anti-human PD-L1 Antibody Shows Increased Detection Sensitivity Compared to E1L3N® Anti-PD-L1 Antibody SP263 anti-PD-L1 antibody (0.44 µg/ml) was applied onto FFPE placenta, tonsil, cervical squamous cell carcinoma, Hodgkin's lymphoma, pancreas adenocarcinoma, prostate adenocarcinoma, skin squamous cell carcinoma and non-small cell lung cancer (NSCLC) tissue samples. Immunohistochemistry was performed on BenchMark Ultra (Ventana Medical System) using StdCC1 cell conditioning with Opt iView detection kit. Corresponding IHC experiments with the E1L3N® antibody were conducted in accordance with the manufacturer's protocols.

Figures 5A, 5B, 5C, 5D, 5E, 5F, 5G, 5H, 5I, 5J:
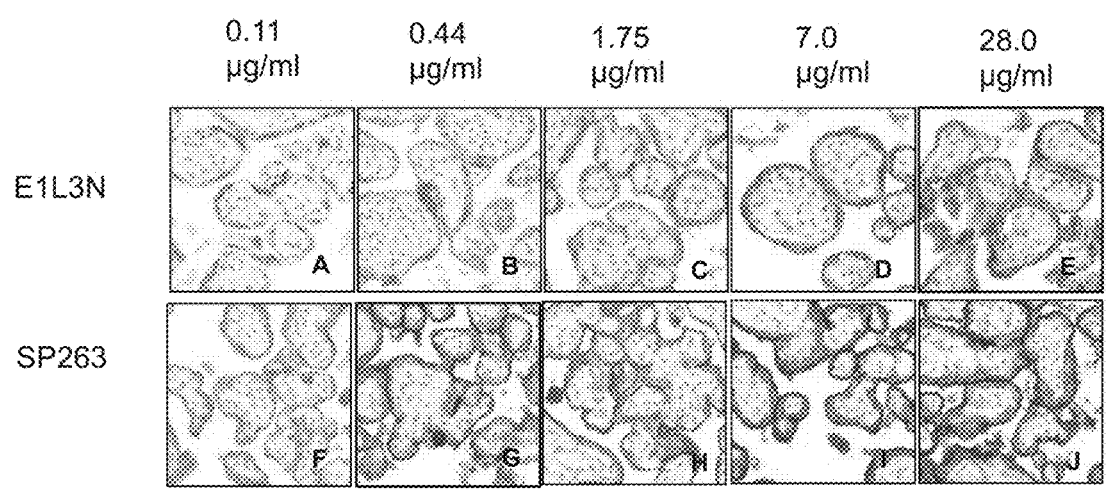
FIG. 5A is an image showing the results of IHC on a FFPE placental tissue section using anti-PD-L1 antibody E1L3N at a concentration of 0.11 µg/ml.
FIG. 5B is an image showing the results of IHC on a FFPE placental tissue section anti-PD-L1 antibody E1L3N at a concentration of 0.44 µg/ml.
FIG. 5C is an image showing the results of IHC on a FFPE placental tissue section using anti-PD-L1 antibody E1L3N at a concentration of 1.75 µg/ml.
FIG. 5D is an image showing the results of IHC on a FFPE placental tissue section using anti-PD-L1 antibody E1L3N at a concentration of 7.0 µg/ml.
FIG. 5E is an image showing the results of IHC on a FFPE placental tissue section using anti-PD-L1 antibody E1L3N at a concentration of 28.0 µg/ml.
FIG. 5F is an image showing the results of IHC on a FFPE placental tissue section using anti-PD-L1 antibody SP263 at a concentration of 0.11 µg/ml.
FIG. 5G is an image showing the results of IHC on a FFPE placental tissue section using anti-PD-L1 antibody SP263 at a concentration of 0.44 µg/ml.
FIG. 5H is an image showing the results of IHC on a FFPE placental tissue section using anti-PD-L1 antibody SP263 at a concentration of 1.75 µg/ml.
FIG. 5I is an image showing the results of IHC on a FFPE placental tissue section using anti-PD-L1 antibody SP263 at a concentration of 7.0 µg/ml.
FIG. 5J is an image showing the results of IHC on a FFPE placental tissue section using anti-PD-L1 antibody SP263 at a concentration of 28.0 µg/ml.

As shown in FIG. 5, both SP263 and E1L3N® were tested at different concentrations. FIGS. 5B-5E show that E1L3N® exhibited detectable staining in FFPE placenta tissue at concentrations as low as 0.44 µg/ml. In contrast, the SP263 antibody generated a moderate to strong signal in FFPE placenta tissue at all tested concentrations (FIGS. 5F-5J). For example, the intensity of the PD-L1 signal in FFPE placenta tissue with the SP263 antibody at 0.44 µg/ml was similar to that observed with the E1L3N® antibody at 28 µg/ml (Compare FIG. 5G with FIG. 5E).

Further, there was a substantial increase in the intensity of the PD-L1 signal generated by the SP263 antibody in tonsil, cervical squamous cell carcinoma, Hodgkin's lymphoma, and skin squamous cell carcinoma tissue samples compared to that observed in the corresponding tissue samples that were incubated with the E1L3N® antibody at the same tested concentration (Compare FIGS. 8G, 8H, 8I and 8L to FIGS. 8A, 8B, 8C and 8F respectively). The PD-L1 signal generated by the SP263 antibody in pancreas adenocarcinoma and prostate adenocarcinoma tissues samples was comparable to that observed with the E1L3N® antibody (Compare FIGS. 8J-8K to FIGS. 8D-E respectively). Finally, the intensity of the PD-L1 signal generated by the SP263 antibody in NSCLC tissue samples was consistently greater than that observed in NSCLC tissue samples that were incubated with the E1L3N® antibody at the same tested concentration (Compare FIGS. 9F-9J to FIGS. 9A-9E).

These results demonstrate that the PD-L1 antibodies of the present disclosure are significantly more sensitive in detecting PD-L1 polypeptide levels in tissue samples compared to other commercially available PD-L1 antibodies that target similar epitopes at the C-terminal region of human PD-L1. Thus, the PD-L1 antibodies of the present disclosure are useful in methods for detecting PD-L1 polypeptide levels in a biological sample and diagnosing cancer in a subject.

EQUIVALENTS

Unless otherwise defined, all technical and scientific terms used herein have the same meaning as commonly understood by one of ordinary skill in the art to which this disclosure belongs.

The disclosures illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

Thus, it should be understood that the materials, methods, and examples provided here are representative of preferred aspects, are exemplary, and are not intended as limitations on the scope of the disclosure.

The disclosure has been described broadly and generically herein. Each of the narrower species and sub-generic groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other aspects are set forth within the following claims.

What is claimed is:

1. An isolated antibody comprising a heavy chain (HC) immunoglobulin variable domain sequence and a light chain (LC) immunoglobulin variable domain sequence, wherein the antibody specifically binds to an epitope of human PD-L1 comprising the amino acid sequence CGIQDTNSKKQSDTHLEET (SEQ ID NO: 1) in formalin-fixed, paraffin embedded tissue with a half maximal effective concentration ($EC_{50}$) of at least $1.5 \times 10^{-11}$ M, wherein:
   the HC comprises
      (a) a HC CDR1 comprising the amino acid sequence NHAIS (SEQ ID NO: 14); and
      (b) a HC CDR2 comprising the amino acid sequence TINSDTHTYYATWPKG (SEQ ID NO: 15); and
      (c) a HC CDR3 comprising the amino acid sequence RIFSSSNI (SEQ ID NO: 16); and
   the LC comprises
      (a) a LC CDR1 comprising the amino acid sequence QASQSIYNNNWLS (SEQ ID NO: 17); and
      (b) a LC CDR2 comprising the amino acid sequence LASTLAS (SEQ ID NO: 12); and
      (c) a LC CDR3 comprising the amino acid sequence IGGESSNNDGIA (SEQ ID NO: 18);
   or an antigen binding fragment thereof.

2. The antibody or antigen binding fragment of claim 1, wherein the HC immunoglobulin variable domain sequence comprises the amino acid sequence of SEQ ID NO: 2.

3. The antibody or antigen binding fragment of claim 1, wherein the LC immunoglobulin variable domain sequence comprises the amino acid sequence of SEQ ID NO: 3.

4. The antibody or antigen binding fragment of claim 1, wherein the HC immunoglobulin variable domain sequence comprises the amino acid sequence of SEQ ID NO: 2, and wherein the LC immunoglobulin variable domain sequence comprises the amino acid sequence of SEQ ID NO: 3.

5. The antibody or antigen binding fragment of claim 1, wherein the antibody is a monoclonal antibody.

6. A composition comprising the antibody or antigen binding fragment of claim 1 bound to a peptide comprising SEQ ID NO: 1.

7. The composition of claim 6 wherein the peptide is a PD-L1 protein.

8. The composition of claim 6, wherein the peptide is associated with a cell.

9. The composition of claim 6, wherein the peptide is bound to a solid support.

10. The composition of claim 6, wherein the peptide is disposed in a solution.

11. The composition of claim 6, wherein the peptide is associated with a matrix.

12. A kit for detecting PD-L1 comprising an antibody or antigen binding fragment of claim 1, and instructions for use.

* * * * *